US010920210B2

(12) United States Patent
Kim et al.

(10) Patent No.: US 10,920,210 B2
(45) Date of Patent: Feb. 16, 2021

(54) RECOMBINANT BATROXOBIN MIXED COMPOSITION AND A HEMOSTATIC POWDER OR HEMOSTATIC PAD COMPRISING SAME

(71) Applicant: NC BIT INC., Gyeonggi-do (KR)

(72) Inventors: Jong Tak Kim, Gangnam-gu Seoul (KR); Young Seomun, Dongjak-gu Seoul (KR); Jin Woo Kim, Suwon-si Gyeonggi-do (KR); Sang Woo Kang, Seoul (KR); Yong Je Woo, Gyeonggi-do (KR); Eun Hye Ko, Seoul (KR)

(73) Assignee: NC BIT INC., Gyeonggi-do (KR)

( * ) Notice: Subject to any disclaimer, the term of this patent is extended or adjusted under 35 U.S.C. 154(b) by 66 days.

(21) Appl. No.: 15/780,974

(22) PCT Filed: Dec. 14, 2016

(86) PCT No.: PCT/KR2016/014679
§ 371 (c)(1),
(2) Date: Jun. 1, 2018

(87) PCT Pub. No.: WO2017/105094
PCT Pub. Date: Jun. 22, 2017

(65) Prior Publication Data

US 2018/0265857 A1 Sep. 20, 2018

(30) Foreign Application Priority Data

Dec. 14, 2015 (KR) ........................ 10-2015-0177952

(51) Int. Cl.

| | |
|---|---|
| *C12N 9/64* | (2006.01) |
| *A61K 47/36* | (2006.01) |
| *A61K 47/42* | (2017.01) |
| *A61K 9/70* | (2006.01) |
| *A61K 38/48* | (2006.01) |
| *C08L 5/08* | (2006.01) |
| *C08L 89/06* | (2006.01) |
| *A61P 7/04* | (2006.01) |
| *A61K 38/00* | (2006.01) |

(52) U.S. Cl.
CPC .............. *C12N 9/6418* (2013.01); *A61K 9/70* (2013.01); *A61K 38/482* (2013.01); *A61K 47/36* (2013.01); *A61K 47/42* (2013.01); *A61P 7/04* (2018.01); *C08L 5/08* (2013.01); *C08L 89/06* (2013.01); *C12Y 304/21074* (2013.01); *A61K 38/00* (2013.01)

(58) Field of Classification Search
None
See application file for complete search history.

(56) References Cited

U.S. PATENT DOCUMENTS 7,939,067 B2 5/2011 Huang
2015/0017225 A1 1/2015 Hubbell et al.

FOREIGN PATENT DOCUMENTS

CN 101705240 B * 7/2012
WO 2009/084841 7/2009

OTHER PUBLICATIONS

Montesino et al. Variation in N-linked oligosaccharide structures on heterologous proteins secreted by the methylotrophic Pichia pastoris. Protein Expression and Purification 14:197-207, 1998.*
Vu et al. Batroxobin binds fibrin with higher affinity and promotes clot expansion to a greater extent than thrombin. JBC 2013, 288(23): 16862-16871.*
Lochnit et al. "Carbohydrate structure analysis of batroxobin, a thrombin-like serine protease from Bothrops moojeni venom" European Journal of Biochemistry, vol. 228, pp. 805-816 (1995).
You "Functional characterization of recombinant batroxobin, a snake venom thrombin-like enzyme, expressed from Pichia pastoris" FEBS Letters, vol. 571, pp. 67-73 (2004).
Soares "Venom-Sweet-Venom: N-Linked Glycosylation in Snake Venom Toxins" Protein and Peptide Letters, vol. 16, pp. 913-919 (2009).
Sartim "Snake venom galactoside-binding lectins: a structural and functional overview" Journal of Venomous Animals and Toxins including Tropical Diseases, vol. 21, No. 35, internal pp. 1-11 (e-pub Sep. 24, 2015).
Meaume, "Snake venoms as modifying agents of blood coagulation" J. Toxicon, 4(1), 25-58, 1966.
Matsui et al., "Snake venom proteases affecting hemostasis and thrombosis" Biochim. Biophys. Acta., 1477;146-156, 2000.
Pirkle H., and Stocker, K. "Thrombin-Like Enzymes from Snake Venoms: An Inventory" Thromb. and Haemostasis, 65(4):444-450 (1991).
Marsh, NA, "Snake venoms affecting the haemostatic mechanism—a consideration of their mechanisms, practical applications and biological significance" Blood Coagul fibrinolysis, vol. 5, 399-410 (1994).
Schumacher et al, "Sensitivity of Experimental Venous and Arterial Thrombosis and Bleeding to Ancrod-Induced Defibrinogenation" Thromb Res, vol. 81(2): 187-194 (1996).

(Continued)

*Primary Examiner* — Iqbal H Chowdhury
(74) *Attorney, Agent, or Firm* — Casimir Jones, SC; Robert A. Goetz

(57) ABSTRACT

The present invention relates to a novel recombinant batroxobin mixture, a hemostatic composition comprising the same, and a method for preparing the same. According to the present invention, the hemostatic composition of the present invention has an excellent hemostatic effect by suppressing rebleeding, and maintains activity thereof even when prepared in a solid form, and thus, the composition of the present invention can be easily used by being applied as a topical hemostatic agent.

13 Claims, 19 Drawing Sheets

Specification includes a Sequence Listing.

(56) References Cited

OTHER PUBLICATIONS

Bell WR Jr., "Defibrinogenating Enzymes" Drugs, 54: 18-31 (1997).
Dempfle et al. "Analysis of fibrin formation and proteolysis during intravenous administration of ancrod" Blood, 96 , 2793-2802 (2000).
Yang et al, "Expression of gloshedobin, a thrombin-like enzyme from the venom of Gloydius shedaoensis, in *Escherichia coli*" Biotechnol Letters, 25:101-104 (2003).
Fan et al., "Cloning, Sequence Analysis and Expression in *E. coli* of the CDNA of the Thrombin-Like Enzyme . . . " Biochem. and Mol Biol Int, 47(2): 217-225 (1999).
Maed et al, "Expression of cDNA for Batroxobin, a Thrombin-Like Snake Venom Enzyme" J. Biochem, 109: 632-637 (1991).

\* cited by examiner

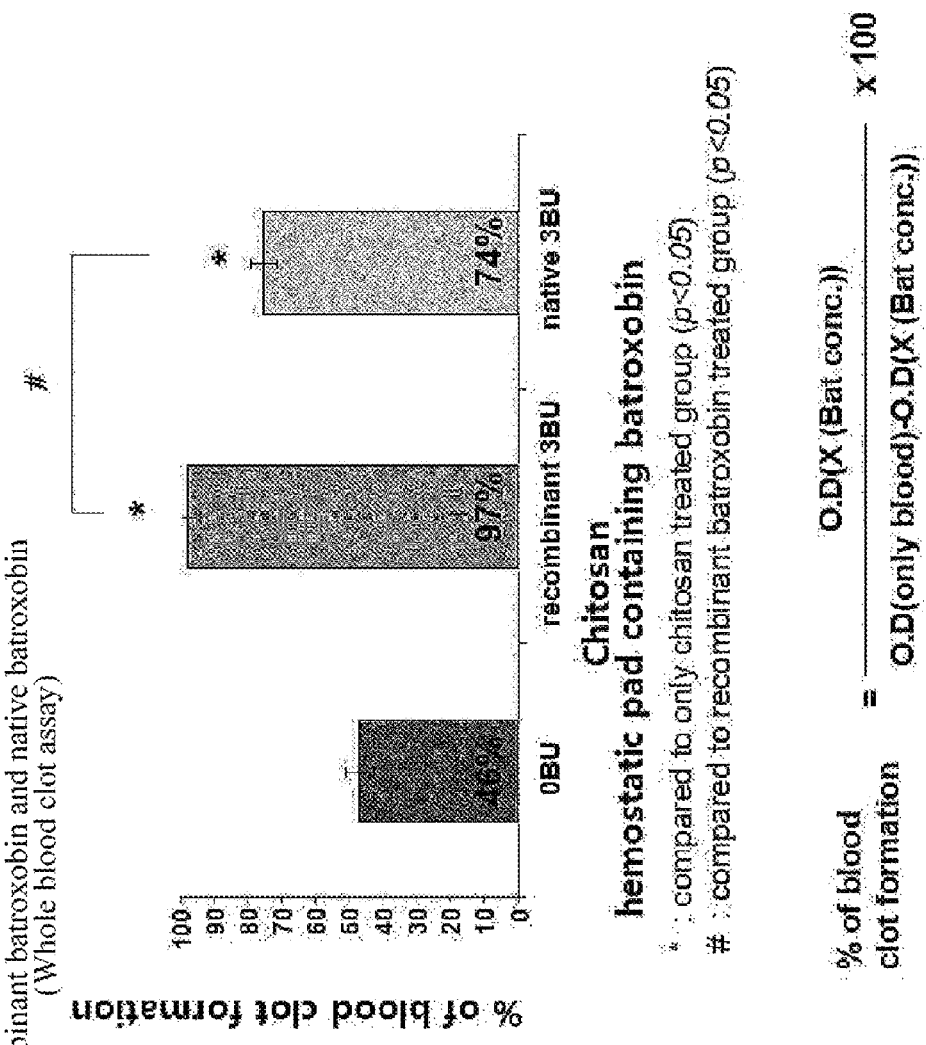

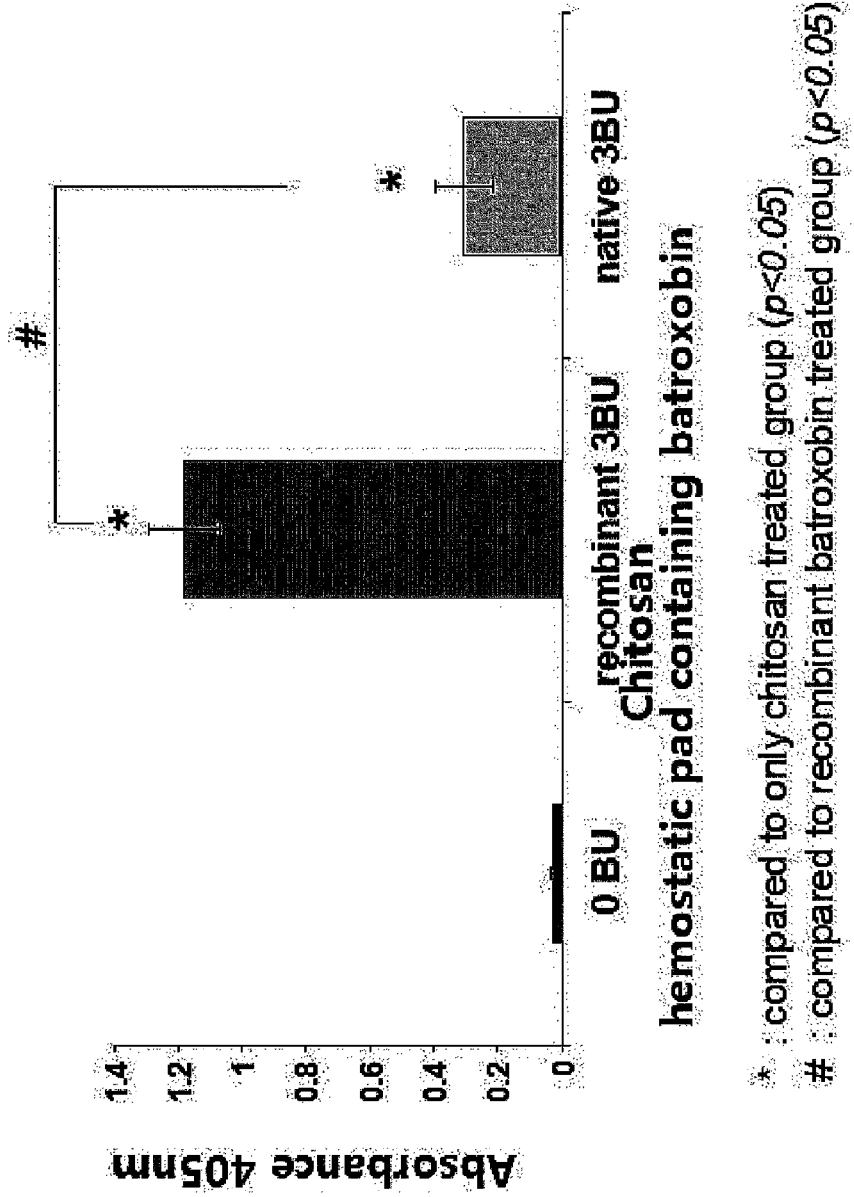

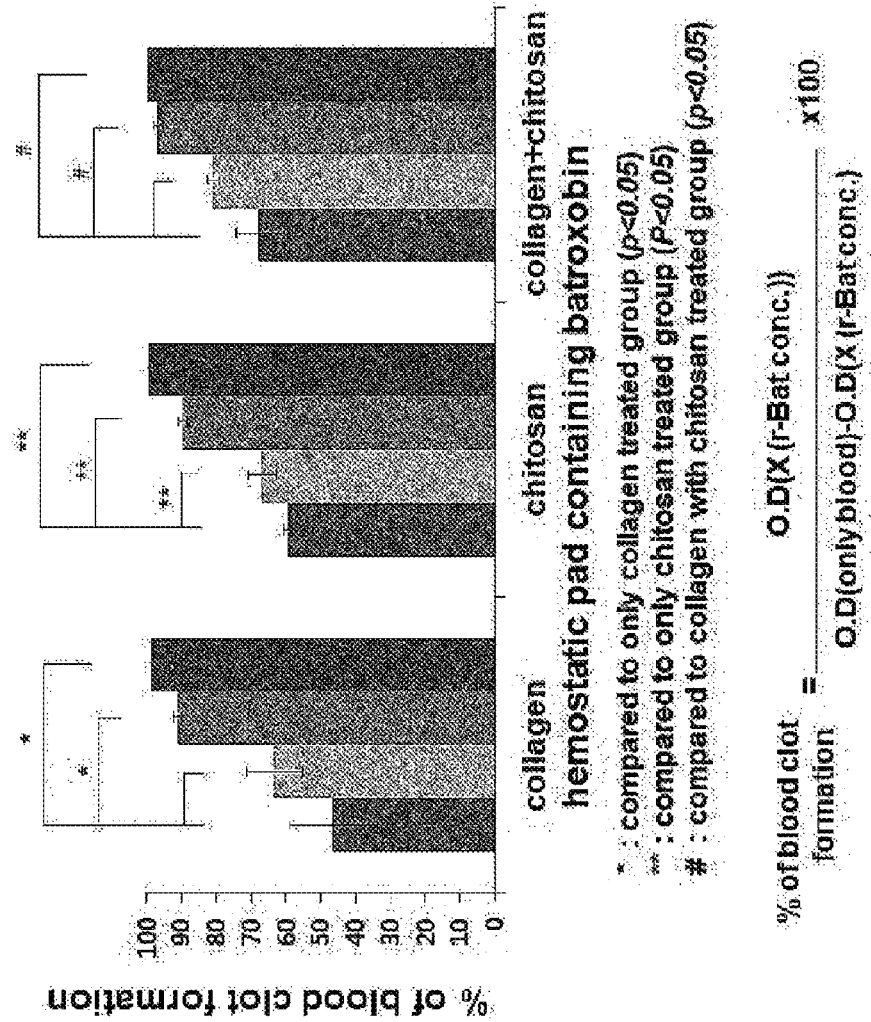

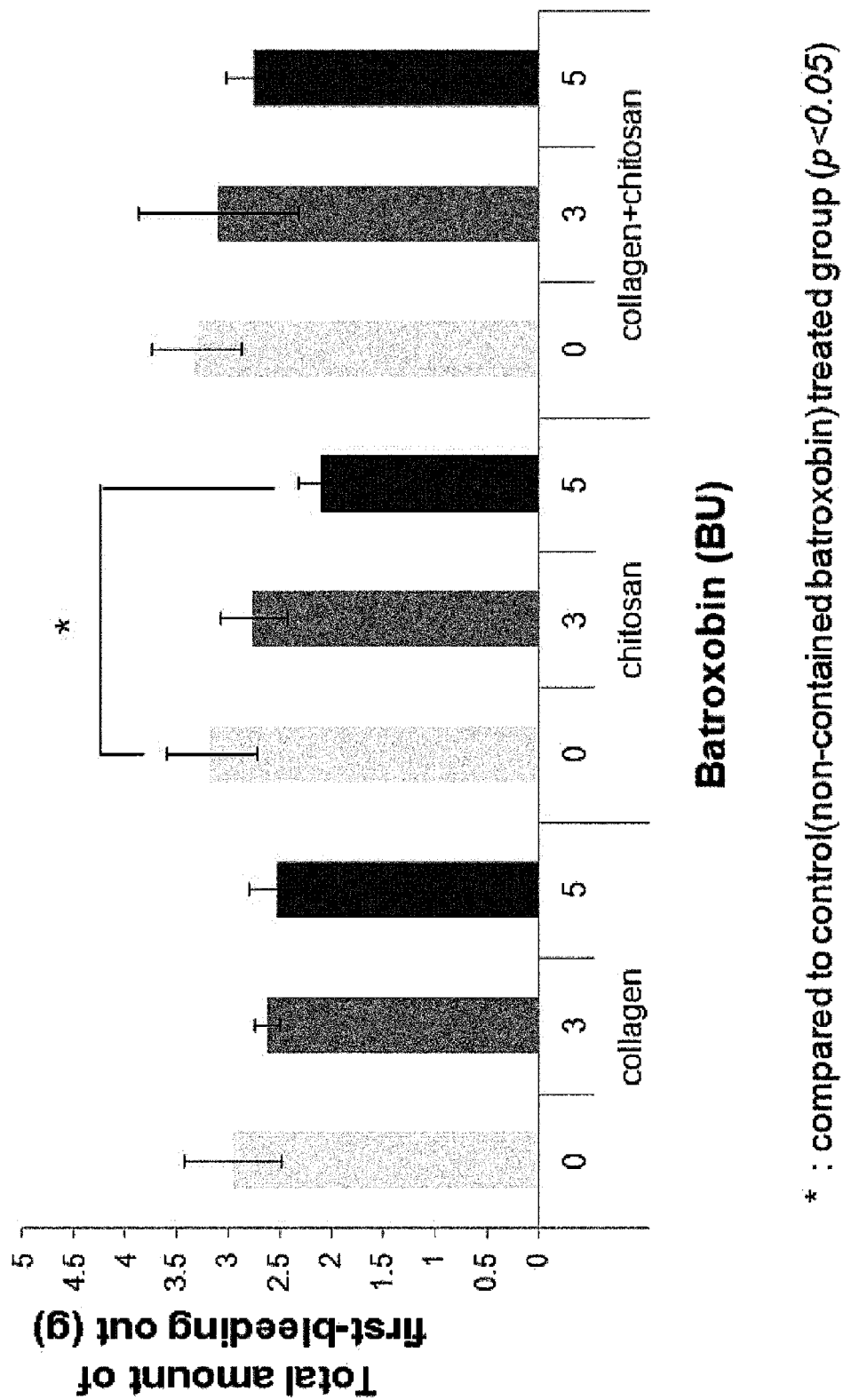

RECOMBINANT BATROXOBIN MIXED COMPOSITION AND A HEMOSTATIC POWDER OR HEMOSTATIC PAD COMPRISING SAME

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 16,000 Byte ASCII (Text) file named "2020-08-19_36386_SQL_ST25" created on Aug. 19, 2020.

TECHNICAL FIELD

This application claims the benefit of Korean Patent Application No. 10-2015-0177952, filed on Dec. 14, 2015, in the Korean Intellectual Property Office, the entire disclosure of which is incorporated herein by reference for all purposes.

The present disclosure relates to a recombinant batroxobin mixed composition that maintains a hemostatic activity even under an acidic condition, and a hemostatic pad including the recombinant batroxobin mixed composition.

BACKGROUND ART

Snake venom effects on a blood coagulation system and a thrombolytic system of mammalian including human has been studied for a long period of time. Several effective components have been isolated and an activity thereof was identified. Various components included in venom are known to directly or indirectly affect fibrin-clotting, platelet aggregation, and the like, to have functions as a procoagulant or an anticoagulant (Meaume., Toxicon, 4;25-58. 1966); Matsui et al., Biochim. Biophys. Acta., 1477: 146-156 (2000)). Some of the components are broadly used for diagnosis and treatment of thrombosis. In particular, at least "20" thrombin-like enzymes that convert fibrinogen into fibrin by cleavage of fibrinopeptide have been reported to date, and cDNA sequences of some of the thrombin-line enzymes were identified.

A thrombin-like enzyme initially hydrolyzes fibrinopeptide A of a fibrinogen molecule to form an unstable fibrin clot (des-A-fibrin) unlike thrombin that is a mammalian native blood coagulation protein, however, the unstable fibrin clot is rapidly degraded by an in vivo fibrinolysis system over time to eventually decrease a blood fibrinogen level (Pirkle, H., and Stocker, K. Thromb Haemost 65;444-450. 1991Marsh, NA, Blood Coagul fibrinolysis, 5; 399-410, 1994).

Based on the above ambivalent enzyme characteristics, the thrombin-like enzyme is used as a hemostatic agent in actual clinical practice or applied as a therapeutic and preventing agent for thrombosis. Since the thrombin-like enzyme does not have an influence on activation of platelets as well as other coagulation factors in blood, an effective hemostatic activity is shown by intravenously or intramuscularly injecting a small amount of the thrombin-like enzyme (2 NIH unit/60 kg) 1 to 2 hours before surgery. On the other hand, it is possible to reduce a blood fibrinogen level without side effects such as bleeding that may occur when using a thrombolytic enzyme, by adjusting a dosage and administration time of the thrombin-like enzyme. Due to a release of des-A-fibrin and fibrinogen degradation products (FDPs) formed during the above process, vascular endothelial cells are stimulated to induce a production of a plasminogen activator. The thrombin-like enzyme is used as a therapeutic and preventing agent for thrombosis by inhibiting a thrombin activity (Schumacher et al, Thromb Res 81;187-194. 1996 Bell W R Jr., Drugs, 54: 18-31. 1997).

Recently, a fibrinogen reduction effect of the thrombin-like enzyme is reported to be effective on treatment of heparin-induced thrombocytopenia or acute ischemic stroke caused by administration of heparin (Dempfle et al. Blood, 96;2793-2802. 2000).

All thrombin-like enzymes that are used in clinical practice are native proteins isolated and purified from snake venom, and representatively include batroxobin isolated from venom of Latin venomous snake *Bothrops atrox moojeni*. Batroxobin is sold exclusively in Swiss Pentapharm Company and is commercially available as trade names such as reptilase (for hemostasis), defibrase (for thrombolysis) and reptilase-reagents (for diagnosis reagents). Also, botropase (for hemostasis, Italian Ravizza Company) purified from venom of Latin venomous snake *Bothrops jararaca*, Malayan pit viper and Ancrod (American Knoll Pharmaceutical company) isolated from venom of *Calloselasma rhodostoma* are also commercially available.

Recently, a Vivostat system (Denmark, Vivosolution company) using batroxobin as an autologous fibrin sealant with the purpose of bleeding prevention and suture in surgical operations also is in the limelight.

However, since native batroxobin is extracted and purified from live snake venom, it is difficult to remove contamination of other venom components in existing snake venom and it is also difficult to supply native batroxobin according to a demand. Also, purification and standardization are difficult due to a severe change in snake venom components by an external environment.

Due to such a limitation in massive production of native batroxobin purified and extracted from snakes, methods of producing recombinant proteins have been studied by various researchers. When eukaryote-derived proteins are expressed in microorganisms, such as *E. coli*, protein expression is reduced due to gene codons with a low translation efficiency of *E. coli* (prokaryotic cells) in a translation process after transcription of eukaryotic genes. To overcome the above phenomenon, a method to improve translation of proteins using a recombinant *E. coli* strain with a foreign eukaryotic tRNA gene to recognize amino acid codes with a low frequency in *E. coli* has been commercialized. Notwithstanding these efforts, inactive proteins are produced during a refolding process of proteins expressed in *E. coli* (Yang et al, Biotechnol Lett, 25;101-104. 2003; Fan et al, Biochem. Mol Biol Int 47;217-225. 1999; Maeda et al, J. Biochem, 109;632-637. 1991). Thus, the present inventors have developed a method of preparing a recombinant batroxobin having a high expression yield and a higher activity than native enzymes, which is disclosed in detail in WO 2009/084841.

However, as reported until now, any example of isolating a recombinant batroxobin mixed composition that exhibits an effect of reducing rebleeding or exhibits an excellent activity by being applied to a hemostatic pad is not reported yet.

Throughout the entire specification, many papers and patent documents are referenced and their citations are represented. The disclosures of the cited papers and patent documents are entirely incorporated by reference into the present specification and the level of the technical field within which the present disclosure falls, and the details of the present disclosure are explained more clearly.

DISCLOSURE OF INVENTION

Technical Subject

The present inventors have made extensive efforts to enable batroxobin to be easily applied to even local hemorrhage. As a result, the present inventors have found that a recombinant batroxobin mixture according to the present disclosure maintains an activity thereof even under an acidic condition, exhibits an excellent activity when the recombinant batroxobin mixture is applied to a hemostatic pad, and is capable of suppressing rebleeding, thereby completing the present disclosure.

An aspect of the present disclosure is to provide a recombinant batroxobin mixed composition.

Another aspect of the present disclosure is to provide a hemostatic composition including a recombinant batroxobin mixed composition.

Other aspects and advantages of the present disclosure will become apparent from the following detailed description together with the appended claims and drawings.

Technical Solution

According to an aspect, there is provided a recombinant batroxobin mixed composition including at least two glycosylated recombinant batroxobins represented by the following Formula 1:

$$M_a\text{-}G_b\text{-}B, \quad [\text{Formula 1}]$$

In Formula 1, M represents a mannose, G represents an N-acetylglucosamine, B represents a recombinant batroxobin, a is an integer of 11 to 13, b is an integer of 1 to 3, $M_a$ represents a straight or branched mannose oligomer, $G_b$ represents a single N-acetylglucosamine or a straight N-acetylglucosamine oligomer, the $M_a$ and the $G_b$ are bound to form a glycosylation structure, and the glycosylation structure is bound to the recombinant batroxobin.

The present inventors have made extensive efforts to enable batroxobin to be easily applied to even local hemorrhage. As a result, the present inventors have found that a batroxobin mixed composition according to the present disclosure maintains an activity thereof even under an acidic condition, exhibits an excellent activity when the batroxobin mixed composition is applied to a hemostatic pad, and is capable of suppressing rebleeding.

As used herein, the term "recombinant batroxobin" refers to a batroxobin prepared in *Pichia pastoris* by mutating a native batroxobin cDNA sequence, and a method of preparing a recombinant batroxobin is disclosed in detail in International Patent Publication No. WO 2009/084841 which is incorporated herein by reference.

As used herein, the term "$M_a$" in Formula 1 refers to a "straight or branched mannose oligomer" in which a is an integer of 11 to 13 as described above, and the term "mannose oligomer" refers to a relatively short mannose chain, that is, a mannose chain including 11 to 13 mannoses, as described above. The mannose oligomer may form a bond in a "straight chain or branched chain." In a straight mannose oligomer, all mannoses except a terminal mannose may form two bonds with adjacent mannoses. In a branched mannose oligomer, a mannose at a position with a branched chain may form a bond to three mannoses. As used herein, the term "$G_b$" refers to a single N-acetylglucosamine in which b is 1, or a straight N-acetylglucosamine oligomer in which b is 2 or 3, as described above. $M_a$ and $G_b$ may form a bond, for example, a covalent bond, which is represented as "$M_a\text{-}G_b$" and is described as a "glycosylation structure" in the present specification. The glycosylation structure may be bound to the recombinant batroxobin via a terminal N-acetylglucosamine to form a "glycosylated recombinant batroxobin" represented by Formula 1. The recombinant batroxobin mixed composition may include at least two recombinant batroxobins that include different glycosylation structures.

According to an example embodiment, the b may be 2. Two N-acetylglucosamines may be bound to form a dimer, one N-acetylglucosamine may form a bond with the mannose oligomer, and the other N-acetylglucosamine may form a bond with the recombinant batroxobin.

According to an example embodiment, the recombinant batroxobin may include an amino acid sequence of SEQ ID NO: 1.

According to an example embodiment, the at least two recombinant batroxobins may have different values of the a. The recombinant batroxobin mixed composition may include a recombinant batroxobin including a glycosylation structure with a different number of mannoses.

According to an example embodiment, the recombinant batroxobin mixture may include three recombinant batroxobins in which the a is 11, 12 and 13. The "including of the three recombinant batroxobins in which the a is 11, 12 and 13" may merely indicate necessarily including the three recombinant batroxobins in which the a is 11, 12 and 13, and may not indicate that a possibility of including a recombinant batroxobin bound to a glycosylation structure including 10 mannoses or less or 14 mannoses or greater is excluded.

According to an example embodiment, the glycosylation structure may be bound to N-terminal amino acid residues at positions 146 and 225 of SEQ ID NO: 1.

According to an example embodiment, a mean molecular weight of recombinant batroxobin molecules included in the recombinant batroxobin mixture may range from 28 kDa to 31 kDa. For example, the mean molecular weight may range from 29.5 kDa to 29.6 kDa.

According to an example embodiment, when the a is 11, the glycosylation structure may have a structure represented by the following Formula 2:

$$\left\{\begin{array}{c} M \\ \quad \diagdown \\ \quad\quad M\text{---}M \\ \quad\quad\diagup \quad\quad \diagdown \\ M \quad\quad M \quad\quad\quad M\text{---}G\text{---}G\text{---}\S \\ \quad\quad\diagdown \quad\quad \diagup \\ \quad\quad M\text{---}M \\ \quad\diagup \\ M\text{---}M \end{array}\right. \quad [\text{Formula 2}]$$

In Formula 2, M represents a mannose, and G represents an N-acetylglucosamine. Throughout the present specification, symbol "{" used to denote a bond between mannoses may indicate that a single mannose or a mannose oligomer located on a left side of the symbol "{" is bound to one of terminal mannoses of the glycosylation structure located on a right side of the symbol "{" without a limitation. As used herein, the term "terminal mannose" refers to one of mannoses located on the right side of the symbol "{" and is located in a terminal of a main chain or a branched chain of the mannose oligomer to form a single bond with another adjacent mannose.

According to an example embodiment, when the a is 12, the glycosylation structure may have a structure represented by the following Formula 3, 4 or 5:

[Formula 3]

$$M-M-M\left\{\begin{array}{c}M\\M-M\\M\\M\\M-M\\M\end{array}\right. M-G-G-\{$$

[Formula 4]

$$M\left\{\begin{array}{c}M\\M-M\\M\\M\\M-M\end{array}\right. M-G-G-\{$$
$$M-M-M$$

[Formula 5]

$$\begin{array}{c}M-M\\M-M\\M-M\\M-M\\M-M\end{array} M-G-G-\{$$

In Formulae 3 through 5, M represents a mannose, and G represents an N-acetylglucosamine.

According to an example embodiment, when the a is 13, the glycosylation structure may have a structure represented by the following Formula 6, 7 or 8:

[Formula 6]

$$M-M-M-M\left\{\begin{array}{c}M\\M-M\\M\\M\\M-M\\M\end{array}\right. M-G-G-\{$$

[Formula 7]

$$M\left\{\begin{array}{c}M-M\\M-M\\M\\M\\M-M\\M-M-M\end{array}\right. M-G-G-\{$$

[Formula 8]

$$M\left\{\begin{array}{c}M-M\\M-M\\M-M\\M-M\\M-M\end{array}\right. M-G-G-\{$$

In Formulae 6 through 8, M represents a mannose, and G represents an N-acetylglucosamine.

According to an example embodiment, the recombinant batroxobin mixture may further include at least one recombinant batroxobin selected from the group consisting of: (a) a recombinant batroxobin including a glycosylation structure with 14 mannoses and two N-acetylglucosamines; (b) a recombinant batroxobin including a glycosylation structure with 15 mannoses and two N-acetylglucosamines; and (c) a recombinant batroxobin including a glycosylation structure with 16 mannoses and two N-acetylglucosamines.

According to another aspect, there is provided a hemostatic composition including the recombinant batroxobin mixed composition.

According to an example embodiment, the hemostatic composition may include 0.5 BU to 20 BU of a recombinant batroxobin mixture. As used herein, the term "BU" refers to a batroxobin unit, and 2 BU indicates a batroxobin amount for coagulation of plasma in 19±0.2 seconds. The BU may be calculated by a titration using a titration standard graph of native batroxobin (NIBSC).

According to an example embodiment, the hemostatic composition may include the recombinant batroxobin mixture in a range of 0.5 to 15 BU, 0.5 to 12 BU, 0.5 to 10 BU, 0.5 to 6 BU, 0.5 to 7 BU, 0.5 to 5.5 BU, 0.5 to 5 BU, 0.8 to 20 BU, 0.8 to 15 BU, 0.8 to 12 BU, 0.8 to 10 BU, 0.8 to 6 BU, 0.8 to 7 BU, 0.8 to 5.5 BU, 0.8 to 5 BU, 1 to 20 BU, 1 to 15 BU, 1 to 12 BU, 1 to 10 BU, 1 to 6 BU, 1 to 7 BU, 1 to 5.5 BU, 1 to 5 BU, 2 to 20 BU, 2 to 15 BU, 2 to 12 BU, 2 to 10 BU, 2 to 6 BU, 2 to 7 BU, 2 to 5.5 BU, 2 to 5 BU, 2.5 to 20 BU, 2.5 to 15 BU, 2.5 to 12 BU, 2.5 to 10 BU, 2.5 to 6 BU, 2.5 to 7 BU, 2.5 to 5.5 BU, 2.5 to 5 BU, 3 to 20 BU, 3 to 15 BU, 3 to 12 BU, 3 to 10 BU, 3 to 6 BU, 3 to 7 BU, 3 to 5.5 BU, 3 to 5 BU, 4 to 20 BU, 4 to 15 BU, 4 to 12 BU, 4 to 10 BU, 4 to 6 BU, 4 to 7 BU, 4 to 5.5 BU, 4 to 5 BU, 4.5 to 20 BU, 4.5 to 15 BU, 4.5 to 12 BU, 4.5 to 10 BU, 4.5 to 6 BU, 4.5 to 7 BU, 4.5 to 5.5 BU, and 4.5 to 5 BU. The hemostatic composition including the recombinant batroxobin mixture may have a volume of 500 μl to 600 μl, of 500 μl to 550 μl, or of 530 μl.

According to an example embodiment, the hemostatic composition may further include a biocompatible polymer. The biocompatible polymer may have a concentration of 0.5 mg/ml to 5 mg/ml. According to an example embodiment, the biocompatible polymer may have a concentration of 0.5 mg/ml to 3 mg/ml, 0.5 mg/ml to 2 mg/ml, 0.5 mg/ml to 1.5 mg/ml, 0.5 mg/ml to 1.2 mg/ml, 0.5 mg/ml to 1 mg/ml, 0.8 mg/ml to 3 mg/ml, 0.8 mg/ml to 2 mg/ml, 0.8 mg/ml to 1.5 mg/ml, 0.8 mg/ml to 1.2 mg/ml, or 1 mg/ml. The biocompatible polymer may be selected from the group consisting of collagen, chitosan, gelatin, albumin, hemoglobin, fibrinogen, fibrin, casein, fibronectin, elastin, keratin, laminin, and derivatives and combinations thereof. In an example, the biocompatible polymer may be collagen, chitosan or a combination thereof. In another example, the biocompatible polymer may be chitosan.

As demonstrated in the following examples, a hemostatic pad including the recombinant batroxobin mixture and the biocompatible polymer (for example, chitosan, collagen or a combination thereof) may have a remarkably high blood coagulation effect due to a high blood clot formation ability, in comparison to a pad including only a biocompatible polymer (FIGS. 2A and 2B).

According to an example embodiment, the hemostatic composition may suppress rebleeding. As demonstrated in the following examples, a hemostatic pad including the recombinant batroxobin mixture and the biocompatible polymer (for example, chitosan, collagen or a combination thereof) may reduce a total amount of bleeding out, may delay a rebleeding time and may significantly reduce an amount of rebleeding out, to suppress rebleeding, in comparison to a pad including only a biocompatible polymer (FIGS. 3 and 4).

According to an example embodiment, the hemostatic composition may be in a form of a solution in an aqueous medium, a suspension, an emulsion, powders, powdered drugs, granules, a sponge, a pad, a patch or a film, however, the form is not limited thereto. For example, the hemostatic composition may be prepared by freeze-drying of a gel, a suspension or a solution, and the gel, the suspension or the solution may need to be prepared by dissolving the biocompatible polymer in an acidic solvent (for example, an acetic acid solution). As demonstrated in the following examples, the activity of the recombinant batroxobin mixture is almost maintained at pH 3.0 and pH 5.0, whereas an activity of a native batroxobin is lowered under the above conditions. Thus, when a hemostatic composition is prepared in a solid form, the activity of the hemostatic composition of the present disclosure may be maintained. For example, the hemostatic composition may be implemented as a hemostatic pad.

According to another aspect, there is provided a method of preparing a recombinant batroxobin hemostatic composition, the method including contacting a recombinant batroxobin with an acidic solution.

According to an example embodiment, the acidic solution may have a pH of 1 to 6. For example, the acidic solution may have a pH of 1 to 5.5, 1 to 5, 2 to 6, 2 to 5.5, 2 to 5, 2.5 to 6, 2.5 to 5.5, 2.5 to 5, 3 to 6, 3 to 5.5, 3 to 5, 3.5 to 6, 3.5 to 5.5, 3.5 to 5, 4 to 6, 4 to 5.5, 4 to 5, 4.5 to 6, 4.5 to 5.5, 4.5 to 5, or 5.

According to an example embodiment, the acidic solution may include a biocompatible polymer.

Since the above description of the hemostatic composition, the recombinant batroxobin and the biocompatible polymer is applicable to the method of preparing the recombinant batroxobin hemostatic composition, redundant description in relation to the hemostatic composition is omitted to avoid excessive complexity of the present specification.

Effect

The features and advantages of the present disclosure are summarized as follows:

(a) the present disclosure provides a recombinant batroxobin mixed composition, a hemostatic composition including the recombinant batroxobin mixed composition, and a method of preparing the recombinant batroxobin mixed composition; and (b) the hemostatic composition may be readily available as a topical hemostatic agent, because the hemostatic composition has an excellent hemostatic effect by suppressing rebleeding and maintains an activity thereof even when the hemostatic composition is prepared in a solid form.

BRIEF DESCRIPTION OF DRAWINGS

FIG. 2A illustrates a whole blood clot assay result for a comparison of blood clot formation effects in a recombinant batroxobin and a native batroxobin. Results of measurement of a ratio (%) of blood clot formation for each experimental group are shown.

FIG. 2B illustrates a fibrinogen assay result for a comparison of blood clot formation effects in a recombinant batroxobin and a native batroxobin. Results of measurement of an absorbance at 405 nm based on blood clot formation for each experimental group are shown.

FIG. 3B is a graph showing a ratio (%) of blood clot formation by using collagen, chitosan and a recombinant batroxobin mixed composition alone or in combination.

FIG. 5B illustrates results of measurement of an amount of first-bleeding out in a femoral artery wound model.

MODE FOR CARRYING OUT THE INVENTION

Figure 1A:
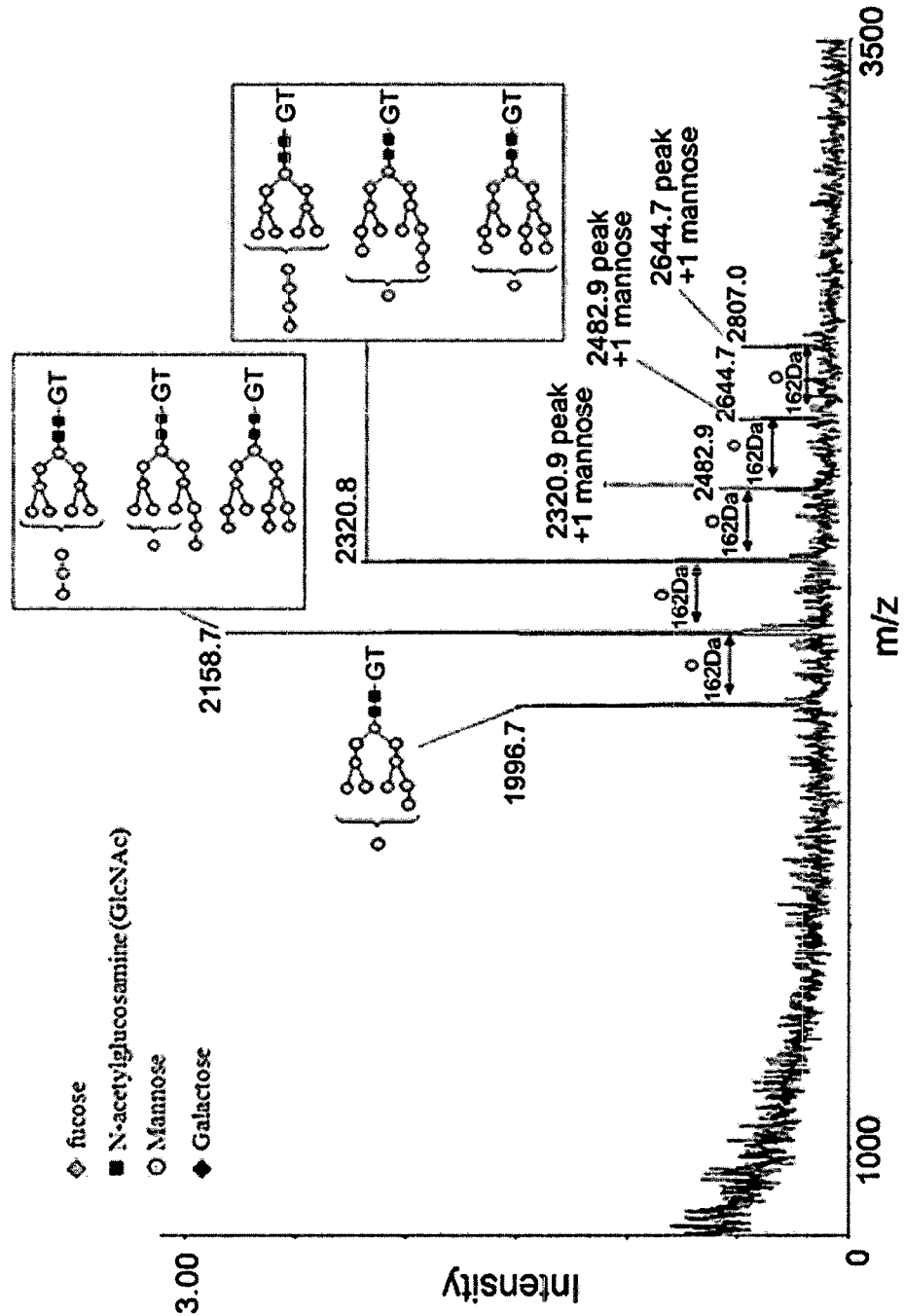
FIG. 1A illustrates a matrix-assisted laser desorption/ionization time-of-flight mass spectrometry (MALDI-TOF MS) analysis result, a second view of FIG. 1B illustrates a liquid chromatography-mass spectrometry (LC-MS) analysis result, and first and third views of FIG. 1B illustrate isoelectric focusing (IEF) analysis results. GT: Glycosylation target; CBB: coomassie blue staining; Zgram: zymogram, showing an activity of rBat; and WB: Western blot.

Hereinafter, the present disclosure will be described in further detail by examples. It would be obvious to those skilled in the art that these examples are intended to be more concretely illustrative and the scope of the present disclosure as set forth in the appended claims is not limited to or by the examples.

EXAMPLES

Example 1. Construction of Recombinant Batroxobin Expression Vector

A recombinant batroxobin used in the present disclosure is batroxobin generated by carrying out mutagenesis in native batroxobin cDNA (SEQ ID NO: 3) to enhance a protein translation efficiency, and a codon sequence was described in SEQ ID NO: 1 (BatSMX). A mutagenesis method is disclosed in detail in International Patent Publication No. WO2009/084841. Also, to increase an efficiency of secreting the recombinant batroxobin into a cell culture medium by expressing the recombinant batroxobin a, a *Pichia pastoris*-optimized synthetic secretion leader gene codon (SMF) was synthesized was synthesized by substituting a *Saccharomyces*-derived α-factor secretion leader gene codon of pPIC9 that is an expression vector of *Pichia pastoris*, and its nucleotide sequence was described in SEQ ID NO: 5.

To fuse a desired recombinant protein at C-terminal of the SMF, the SMF was inserted into a multicloning site of pUC118HincII/BAP (Takara Bio Inc., Japan), which was named as pSMF. Since a XhoI nucleotide sequence (CTC GAG) used in a cloning site of C-terminal of a native α-factor secretion leader sequence that was conventionally commercialized encodes a Leu codon, in particular, a codon (ctc) with a low transcription efficiency, a PCR was performed by using the SMF as a template, and using SMF-R (5'-TAACTCTTTTTTC-CAAAGAAACACCTTCTTCCTTTGCTGC-3') (SEQ ID NO.: 8) that is a C-terminal primer overlapped with N-terminal of batroxobin, and SMF-F (5'-GGATCCAAACGAT-GAGATTTCCAT-3') (SEQ ID NO.: 9) that may generate a BamHI sequence at N-terminal of a recombinant SMF gene cassette, while replacing a nucleotide sequence of GTA-TCT-CTC-GAG (SEQ ID NO.: 12) for Val80-Ser81-Leu82-Glu83 with that of GTT-TCT-TTG-GAA (SEQ ID NO.: 13).

N-terminal encoding nucleotide sequences of the following BatSMX were designed using primers corresponding to an overlap sequence (amino acid sequence: L E K R/V I G D E) (SEQ ID NO.: 14) consistent with codons modified at C-terminal of the SMF. A PCR was performed by using BatSMX as a template and using SMX-F (5'-CTTTG-GAAAAAAGAGTTATTGGTGGTGATGAA-3') (SEQ ID NO.: 10) as an N-terminal extension primer in BatSMX and SMX-R (5'-GCGGCCGCTTATGGACAAGT-3') (SEQ ID NO.: 11) as a C-terminal primer.

The resulting SMF and PCR products of batroxobin genes were mixed, and N-terminal primers used in SMF modification and C-terminal primers used in batroxobin modification were mixed. An assembly PCR was performed and then cloned into pTOP Blunt vector (Enzynomics, Korea) to complete SMFBatSMX that is a gene cassette in which codons of an α-factor secretion leader sequence of an SMF gene and batroxobin gene are optimized. The above genes were treated with BamHI-NotI restriction enzymes, and BamHI-NotI fragments (970 bp) were recovered and subcloned into pPIC9 that is a *Pichia* expression vector, to construct pSMFBatSMX that is an expression vector.

Example 2. Isolation of Recombinant Batroxobin

After transformation into a *Pichia pastoris* strain (GS115, Invitrogen) under a voltage condition of 1.5 kV using an electroporator (Bio-Rad Gene Pulser, USA), a selection was performed on a histidine-deficient yeast nitrogen base (YNB) solid medium. A single colony obtained by the selection was inoculated into 1 L of Buffered Minimal Glycerol (BMG) liquid media (100 mM sodium phosphate (pH 6.0), 1.34% yeast nitrogen base, 4×10-5% biotin, and 1% glycerol) and incubated with shaking at 30° C. An expression of recombinant proteins via an Alcohol Oxidase 1 (AOX1) promoter was induced by adding 0.1% methyl alcohol every 24 hours in a cell density in which an absorbance reached about 1.0 at 600 nm, and culturing was performed. A culture solution was harvested by centrifuging the culture at 5,000×g and loaded into a column (1.3×20 cm) packed with phenyl-sepharose (GE Healthcare, USA) equilibrated with a 2.5 M ammonium sulfate solution. A fraction with an enzyme activity of the recombinant batroxobin was eluted at a flow rate of 0.5 ml/min using a linear gradient of 2.5-0 M ammonium sulfate solution, to isolate the recombinant batroxobin.

Example 3. Analysis of Structure of Isolated Recombinant Batroxobin Mixture 3-1. Analysis of Glycosylation Pattern of Recombinant Batroxobin Using Matrix-Assisted Laser Desorption/Ionization Time-Of-Flight Mass Spectrometry (MALDI-TOF MS)

For TCA precipitation, a 50% TCA solution was added to 50 μg of the recombinant batroxobin to have a final batroxobin concentration of 10%, and stored on ice for 30 minutes. Centrifugation was performed at 12,000 rpm, at 4° C. for 10 minutes, to eliminate all the remaining solution except protein precipitates. 500 μl of a cold acetone solution was added and vortexing was performed for about 3 minutes, followed by centrifugation at 12,000 rpm, at 4° C. for 10 minutes. The remaining solution except protein precipitates was eliminated and completely dried at room temperature. 10 μl of a 5 M Urea solution was added to the protein precipitates and stored at room temperature for 10 minutes while shaking, and then 40 μl of a 0.1 M ABC buffer solution was added and mixed, to prepare a sample for a MALDI-TOF MS.

2 IU PNGase-F was added to the sample prepared by the TCA precipitation, and the sample was stored at 37° C. for 16 hours. The sample was loaded in a PGC column and 300 μl of the sample was eluted in a 40% ACN/0.05% TFA buffer solution. An eluted solution was dried by SpeedVac (Bio-Tron, Korea), and the dried sample was dissolved in 10 μl of distilled water. DOWEX-50W (Sigma, USA) as an ion exchange resin was added, vortexing was performed for 1 hour and the DOWEX-50W was removed, followed by drying by SpeedVac. 10 μl of dimethyl sulfoxide (DMSO) and 10 μl of methyl iodide were added to the dried sample and stored at room temperature for 12 hours, followed by drying by SpeedVac. 30 μl of a GT solution (1 mg/mL of 1% acetic acid/99% methanol [v/v]) was added and stored at room temperature for 4 hours, followed by drying by Speed-Vac. The dried sample was mixed with 2 μl of a 2,5-DHB solution (30 mg/mL of 70% acetonitrile/30% water [v/v]), and 1 μl of a mixed solution was spotted on a stainless steel MALDI plate and dried at room temperature, to perform measurement by MALDI-TOF.

As a result, it was confirmed that the recombinant batroxobin according to the present disclosure shows 3 major glycosylation patterns and 3 miner glycosylation patterns (FIG. 1A). Also, it was confirmed that a mannose is mainly used as sugar for glycosylation, that each pattern is determined by an additional bind of a mannose, and that the N-acetylglucosamine is also used.

3-2. Analysis Using Liquid Chromatography-Mass Spectrometry (LC-MS)

A sample for an LC-MS analysis was prepared by TCA precipitation in the same manner as in Example 3-1.

10 μl of the sample was inserted into a liquid chromatograph mass spectrometer and an analysis was performed using reverse phase LC-ESIMS. The total time for the analysis was 40 minutes.

Recombinant batroxobin proteins were isolated on ZORBAX 300SBC18 (1×150 mm, 3.5 μm, Agilent, USA). To isolate the recombinant batroxobin protein, a mobile phase solvent A [0.2% (v/v) formic acid (FA) aqueous solution] and a mobile phase solvent B [100% acetonitrile (ACN)/ 0.2% (v/v) FA aqueous solution] were used at a flow rate of 35 μl/min. Proteins isolated by an HPLC were coupled to an ESI source of a QTOF MS, to measure mass values of protein ions.

As a result, it was confirmed that the recombinant batroxobin has a mass of 29.548 kDa on average and has a mass of about 25.5 kDa after removing of sugar.

3-3. Analysis Using Isoelectric Focusing (IEF)

The recombinant batroxobin sample isolated in Example 2 was added to an IEF sample buffer solution (2×, Komabiotech, Korea) and mixed. An IEF Cathode buffer solution (10×, Komabiotech, Korea) was diluted in deionized water at a ratio of 1:9 and added to an IEF upper chamber, and an IEF Anode buffer solution (50×, Komabiotech, Korea) was diluted in deionized water at a ratio of 1:49 and poured into an IEF lower chamber. 2 μg of the sample mixed with the IEF sample buffer solution was loaded in a well filled with the IEF Cathode buffer solution. The sample was transferred, gels were removed from a cassette and fixed in a fixing solution (12% TCA) for 30 minutes. IEF gels were stained using Coomassie brilliant blue and de-stained using a destain solution.

Figure 1B:
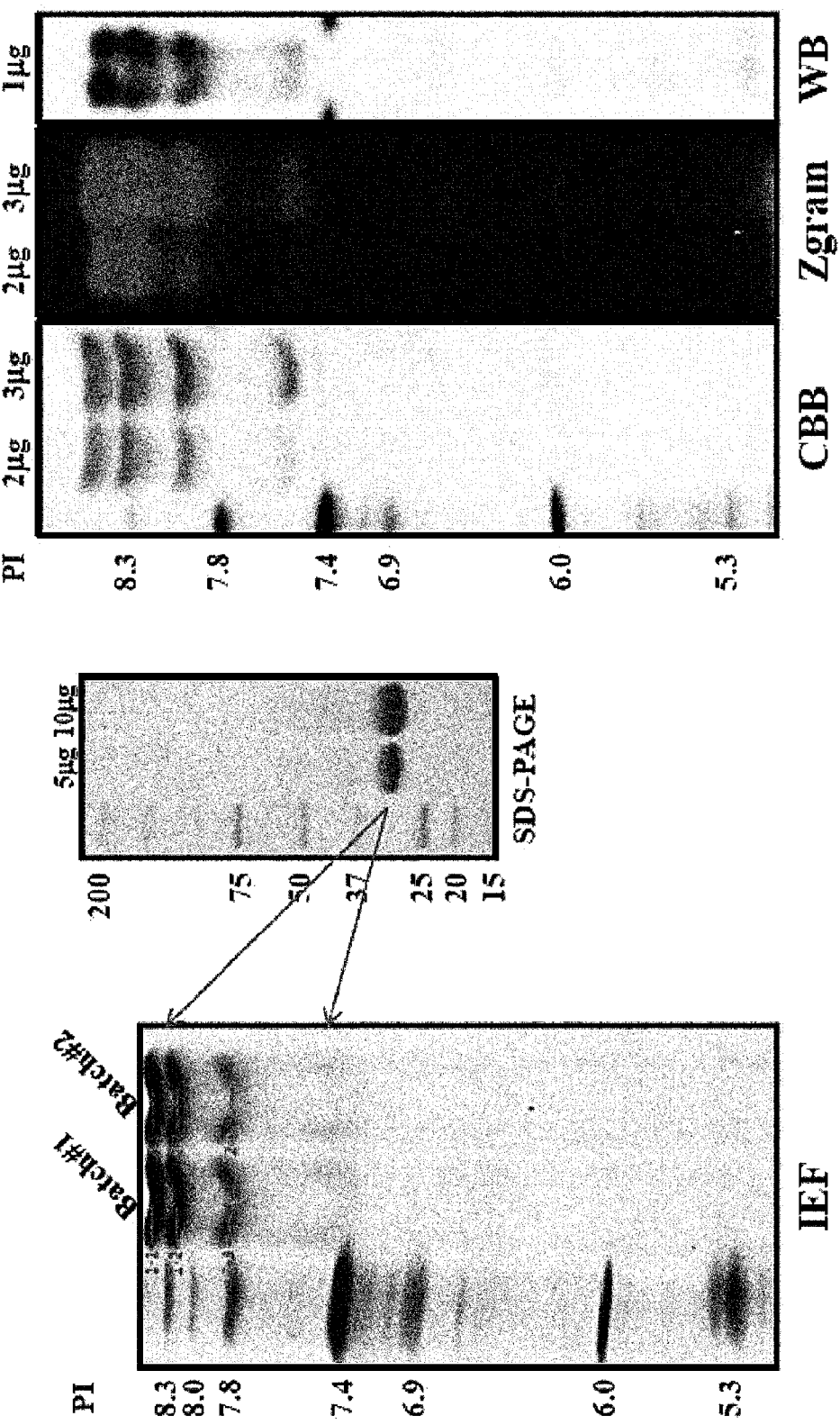
FIG. 1 illustrates a structure of a recombinant batroxobin according to the present disclosure and a structure analysis result.

As a result, it was confirmed that the recombinant batroxobin has 3 bands (bands of the major glycosylation patterns of FIG. 1A) at pI 7.8 or higher and 1 band (a band of the miner glycosylation pattern of FIG. 1B) around pI 7.4 (FIG. 1B). The recombinant batroxobin differs from the native batroxobin in that the native batroxobin has a pI of about 6.6 and only a single band.

Example 4. Analysis of Activity Based on pH of Isolated Recombinant Batroxobin Mixture S-2238 (Biophen, USA) that is a thrombin substrate was purchased and dissolved at a concentration of 10 mM. During measurement of batroxobin activity, a final concentration of 0.1 mM was measured and 50 mM Tris-cl, pH 7.5, was added for dilution.

Each of the recombinant batroxobin and the native batroxobin (NIBSC, UK) was allowed to have a concentration of 10 BU/ml and was diluted with buffer solutions for each pH (pH 3, 5, 7 and 9), to obtain a concentration of 5 BU/ml.

Samples prepared with the concentration of 5.0 BU/ml were classified and stored at 4° C. and 37° C., 20 μl of each of a standard sample and a measurement sample was added onto a 96-well plate, 180 ul of the thrombin substrate containing the 50 mM Tris-cl, pH 7.5 was added to each of the samples, to measure an absorbance at 405 nm at 37° C. for 20 minutes using an ELISA.

TABLE 1

|  |  | Incubation time 24 hours Temperature | | | |
| --- | --- | --- | --- | --- | --- |
|  |  | 4° C. | | 37° C. | |
|  |  | Batroxobin | | | |
|  |  | rBat | nBat | rBat | nBat |
| Buffer solution | KPi pH 3.0 | 83.1 | 41.4 | 80.7 | 40.2 |
|  | Glycine pH 3.0 | 80.7 | 40.2 | 80.7 | 39.0 |
|  | KPi pH 5.0 | 95.1 | 80.8 | 95.1 | 72.4 |
|  | Acetic acid pH 5.0 | 104.7 | 74.8 | 104.7 | 72.4 |
|  | NaPi pH 7.0 | 104.7 | 96.3 | 99.9 | 95.2 |
|  | Tris pH 7.0 | 102.3 | 105.9 | 97.5 | 92.8 |
|  | Glycine pH 9.0 | 97.5 | 86.8 | 95.1 | 82.0 |
|  | Tris pH 9.0 | 90.3 | 77.2 | 90.3 | 62.9 |

Example 5. Preparation of Hemostatic Pad with Batroxobin 5 mg of atelocollagen fibers (Sigma, USA) extracted from bovine and 5 mg of chitosan powder (Sigma, USA) extracted from shells of shrimp were each dissolved in 500 μl of a 0.5 M acetic acid solution at 4° C. for about 24 hours. A group containing batroxobin in 1% (w/v) collagen (5 mg of collagen/500 μl of a 0.5 M acetic acid solution), a group containing batroxobin in 1% (w/v) chitosan (5 mg of chitosan/500 μl of a 0.5 M acetic acid solution), and a group containing batroxobin in 1% (w/v) collagen (2.5 mg of collagen/250 μl of a 0.5 M acetic acid solution) and 1% (w/v) chitosan (2.5 mg of chitosan/250 μl of a 0.5 M acetic acid solution) were dissolved by adding the recombinant batroxobin solution isolated in Example 1 at concentrations of 1 BU, 2 BU, 3 BU and 5 BU after 23 hours. To remove foam formed during a dissolving process, each solution was subject to a degassing process by centrifugation at 3,000 rpm, at 4° C. for 10 minutes. 500 μL of each of the remaining solutions from which the form was removed was added to a 24-well plate on an ice pack to maintain a low temperature, and frozen in a −80° C. quick-freezer for 48 hours. Here, a bottom surface was kept flat to prevent the solutions from leaning to one side. The frozen solutions were freeze-dried for 48 hours in a −50° C. freeze dryer (ALPHA 1-2 LD plus, CHRIST, Germany), to prepare a pad (a circular pad, 15 mm in diameter and 3 mm in thickness).

Prepared pads are shown in Table 2 below.

TABLE 2

|  | Collagen pad | Chitosan pad | Pad with Collagen and Chitosan |
| --- | --- | --- | --- |
| Comparative group | 1% collagen | 1% chitosan | 1% collagen + 1% chitosan |
| Experimental group 1 | 1% collagen + 1 BU of batroxobin | 1% chitosan + 1 BU of batroxobin | 1% collagen + 1% chitosan + 1 BU of batroxobin |

TABLE 2-continued

|  | Collagen pad | Chitosan pad | Pad with Collagen and Chitosan |
| --- | --- | --- | --- |
| Experimental group 2 | 1% collagen + 2 BU of batroxobin | 1% chitosan + 2 BU of batroxobin | 1% collagen + 1% chitosan + 2 BU of batroxobin |
| Experimental group 3 | 1% collagen + 3 BU of batroxobin | 1% chitosan + 3 BU of batroxobin | 1% collagen + 1% chitosan + 3 BU of batroxobin |
| Experimental group 4 | 1% collagen + 5 BU of batroxobin | 1% chitosan + 5 BU of batroxobin | 1% collagen + 1% chitosan + 5 BU of batroxobin |

Example 6. Comparison Between Hemostatic Pad with Native Batroxobin and Hemostatic Pad with Recombinant Batroxobin A hemostatic pad containing 3 BU of native batroxobin and 1% chitosan and a hemostatic pad containing 3 BU of the recombinant batroxobin and 1% chitosan were prepared and effects of the hemostatic pads were compared. Prepared hemostatic pads include 1% chitosan for all groups, a non-treated group was used as a control group, and a group containing 3 BU of the native batroxobin and a group containing 3 BU of the recombinant batroxobin were used as experimental groups. Experimental results were shown as a blood clot formation test and a pad fibrin formation test.

Sprague-Dawley (SD) rats (Oriental Bio, Korea) of about 350 g were anesthetized using 30 mg/kg of Zoletil (Boehringer Ingelheim Agrovent, Denmark) and 10 mg/kg of Rompun (Bayer, Canada), and blood was collected at a ratio of 1:4 (sodium citrate:rat blood) from an abdominal vena cava using a syringe containing 0.109 M sodium citrate by an abdominal incision.

400 µL of blood was added to the prepared pads, followed by reaction for 10 minutes with stirring in a 37° C. incubator. 400 µL, of phosphate buffer saline (PBS, Wellgene, Korea) was added to dissolve non-coagulated blood, and an absorbance was measured at 540 nm using a spectrophotometer (SpectraMax microplate reader, Molecular devices, USA) to measure a hemoglobin concentration using a Drabkin's reagent (FIG. 2A).

A 20 mM Tris-HCl buffer with pH 7.5 was added to the prepared pads, followed by reaction for 10 minutes with stirring in a 37° C. incubator. Batroxobin isolated from the pads was added to a warmed 0.9% saline buffer containing prepared fibrinogen of 10 mg/ml, followed by reaction for 10 minutes with stirring in a 37° C. incubator. To obtain experiment results, an absorbance was measured at 405 nm using a spectrophotometer (FIG. 2B).

Example 7. Analysis of Blood Clot Formation of Hemostatic Pad

Sprague-Dawley (SD) rats (Oriental Bio, Korea) of about 350 g were anesthetized using 30 mg/kg of Zoletil (Boehringer Ingelheim Agrovent, Denmark) and 10 mg/kg of Rompun (Bayer, Canada), and blood was collected at a ratio of 1:4 (sodium citrate:rat blood) from an abdominal vena cava using a syringe containing 0.109 M sodium citrate by an abdominal incision. 400 µL of blood was added to the prepared pads, followed by reaction for 10 minutes with stirring in a 37° C. incubator. 400 µL of phosphate buffer saline (PBS, Wellgene, Korea) was added to dissolve non-coagulated blood, and an absorbance was measured at 540 nm using a spectrophotometer (SpectraMax microplate reader, Molecular devices, USA) to measure a hemoglobin concentration using a Drabkin's reagent.

For hemostatic pads, a non-treated group was used as a control group and 12 groups except the control group were used. In the 12 groups, 3 comparative groups were a group of 1% collagen, a group of 1% chitosan and a group of 1% collagen and 1% chitosan, and experimental groups were groups containing 1, 2 and 3 BU of batroxobin in 1% collagen, groups containing 1, 2 and 3 BU of batroxobin in 1% chitosan, and groups containing 1, 2 and 3 BU of batroxobin in 1% collagen and 1% chitosan.

Figure 3A:
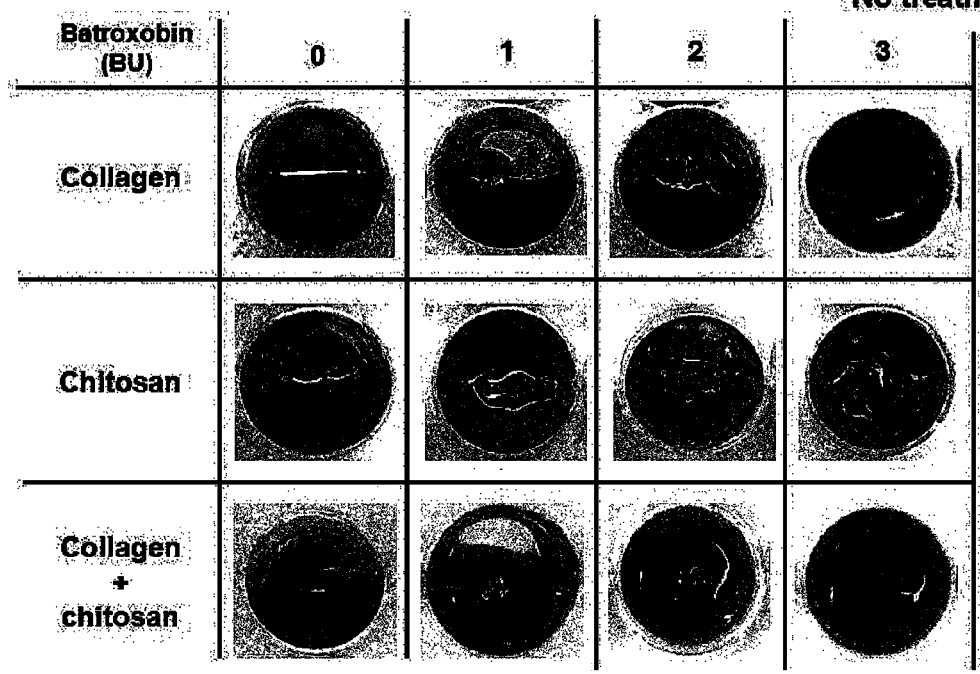
FIG. 3A illustrates states of blood clot formation by using collagen, chitosan and a recombinant batroxobin mixed composition alone or in combination.

When blood coagulation degrees were observed with the naked eye, it was confirmed that the blood coagulation degrees in all the groups were increased in comparison to that of the non-treated group. When the blood coagulation degrees were observed with the naked eye by tilting a well plate by about 15°, about half of a blood volume was seemed to be coagulated in the comparative groups. It was found that the blood coagulation degree was considerably increased as a concentration of batroxobin increased from 1 BU to 3 BU in each of the comparative groups. In particular, in 7 groups, that is, a group containing 3 BU of batroxobin in collagen, a group containing 3 BU of batroxobin in chitosan, a group containing 2 BU of batroxobin and 3 BU of batroxobin in collagen and chitosan, it was observed with the naked eye that blood clots were formed in forms of dark lumps and that blood does not flow because blood was almost completely solidified (FIG. 3A).

Since a high hemoglobin concentration was measured based on an increase in an amount of non-coagulated blood, a concentration of hemoglobin in blood was measured using a Drabkin's reagent, calculated in reverse and converted to percentage (%), to evaluate a degree of blood clot formation. Based on results of the above evaluation using a graph, it was found that the degree of blood clot formation was about 50% in a collagen group, the degree of blood clot formation was about 60% in a chitosan group and the degree of blood clot formation was about 65% in a group with collagen and chitosan. In each comparative group, the degree of blood clot formation was increased as the concentration of batroxobin increases. It was confirmed that the degree of blood clot formation was considerably increased over about 90% in groups containing 2 BU of batroxobin and that the degree of blood clot formation was almost 100% in groups containing 3 BU of batroxobin (FIG. 3B).

Based on results in the above experiment, it was confirmed that the hemostatic pads including batroxobin together with collagen or chitosan allow blood clots to be rapidly formed to stop bleeding in comparison to the hemostatic pad including only either collagen or chitosan. Also, it was found that a sufficient hemostatic effect may be obtained even with only 3 BU of batroxobin by Example 5.

Example 8: Hemostatic Effect in Femoral Artery Wound Model

Figure 4A:
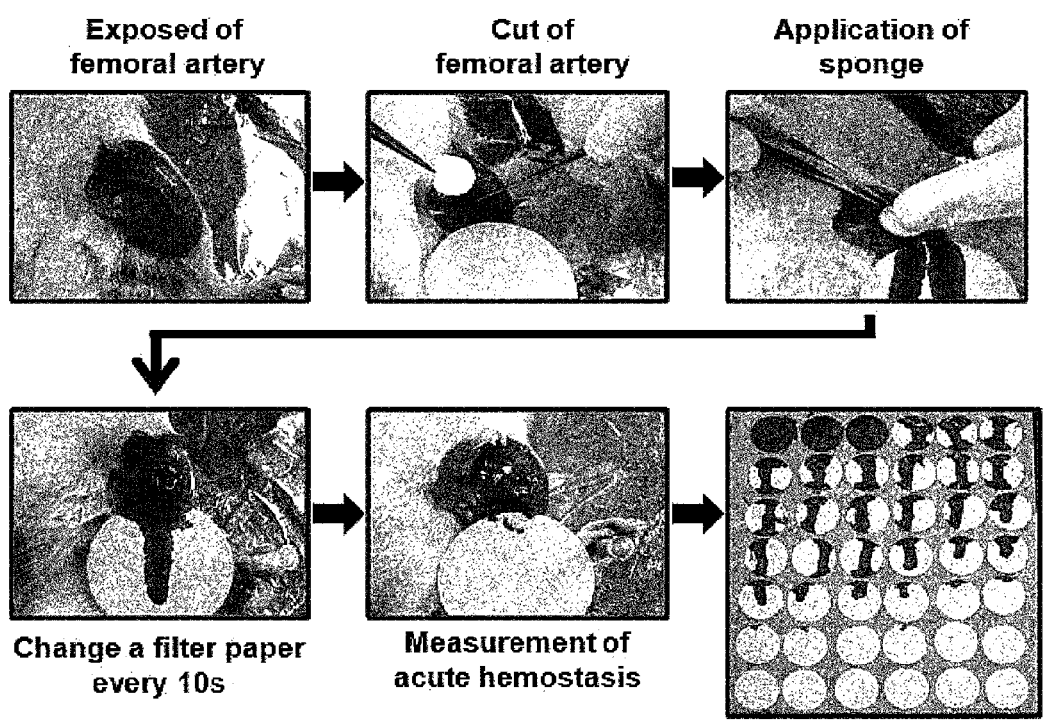
FIG. 4A illustrates a hemostatic effect experiment process over time in a femoral artery wound model.
Figure 4B:
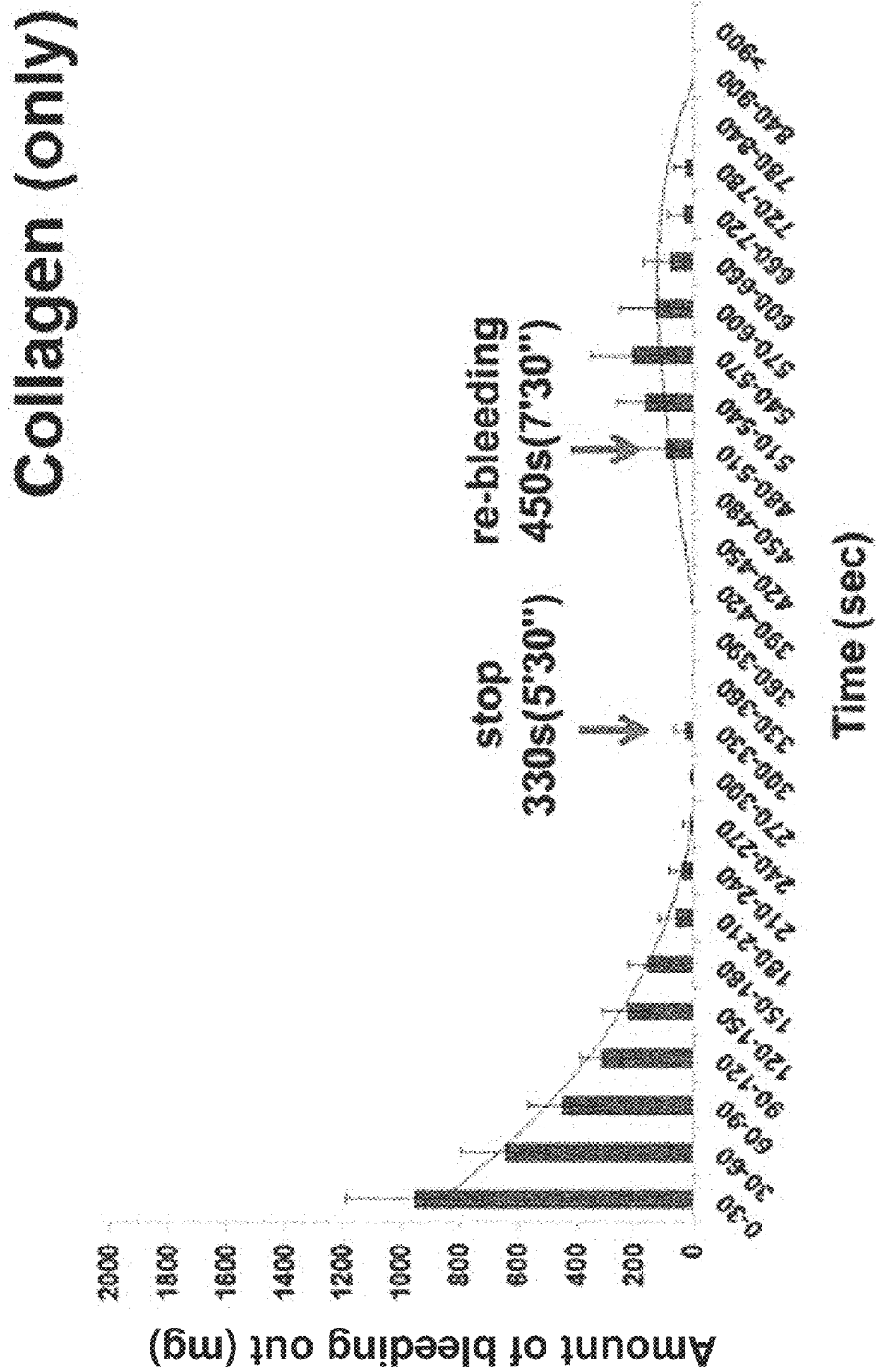
FIG. 4B illustrates a hemostatic effect and rebleeding measurement results when collagen is used alone in a femoral artery wound model. Experimental results are shown in a graph of an amount of bleeding out over time.
Figure 4C:
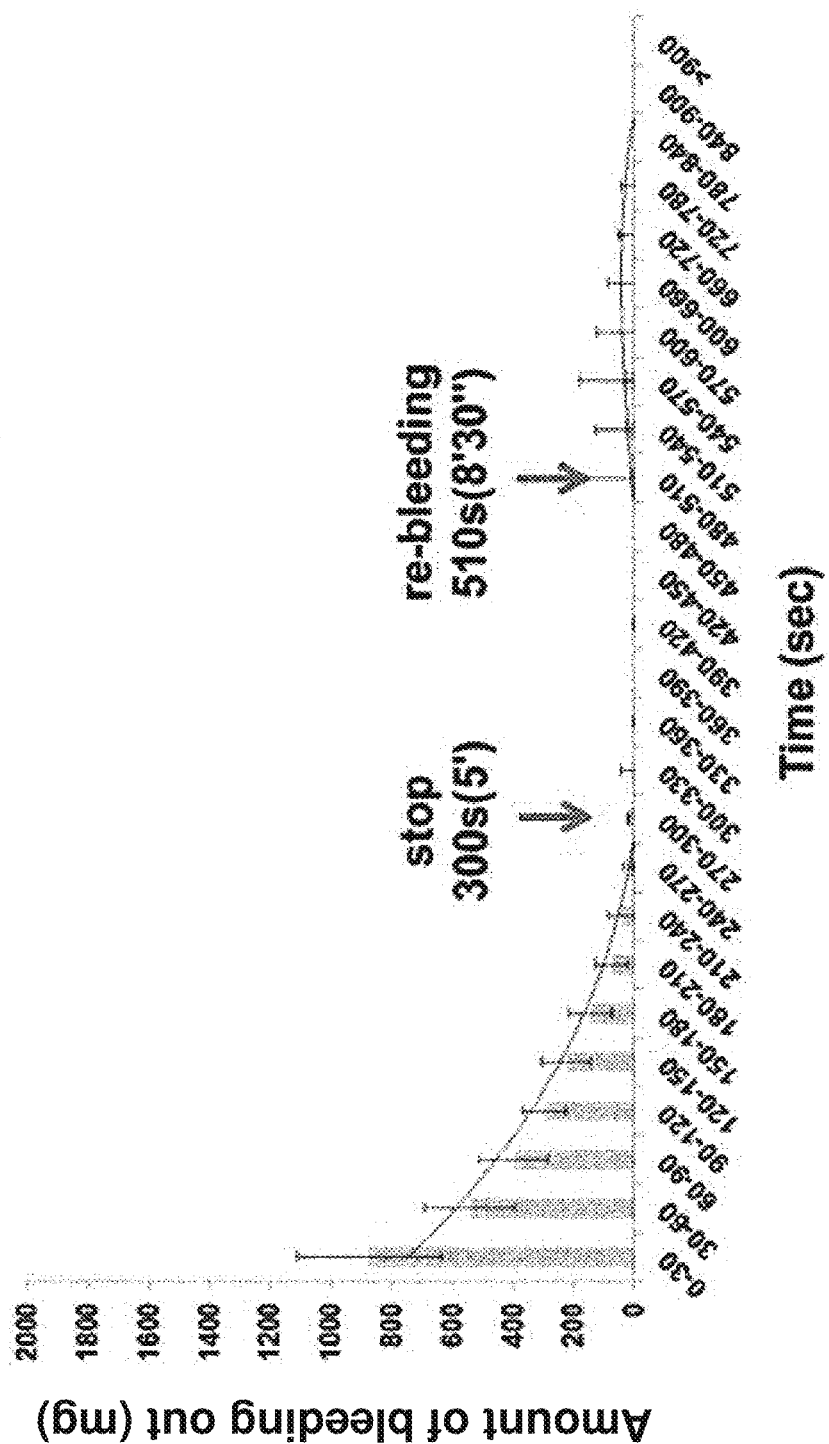
FIG. 4C illustrates a hemostatic effect and rebleeding measurement results when a combination of collagen and 3 BU of a recombinant batroxobin mixed composition is used in a femoral artery wound model. Experimental results are shown in a graph of an amount of bleeding out over time.
Figure 4D:
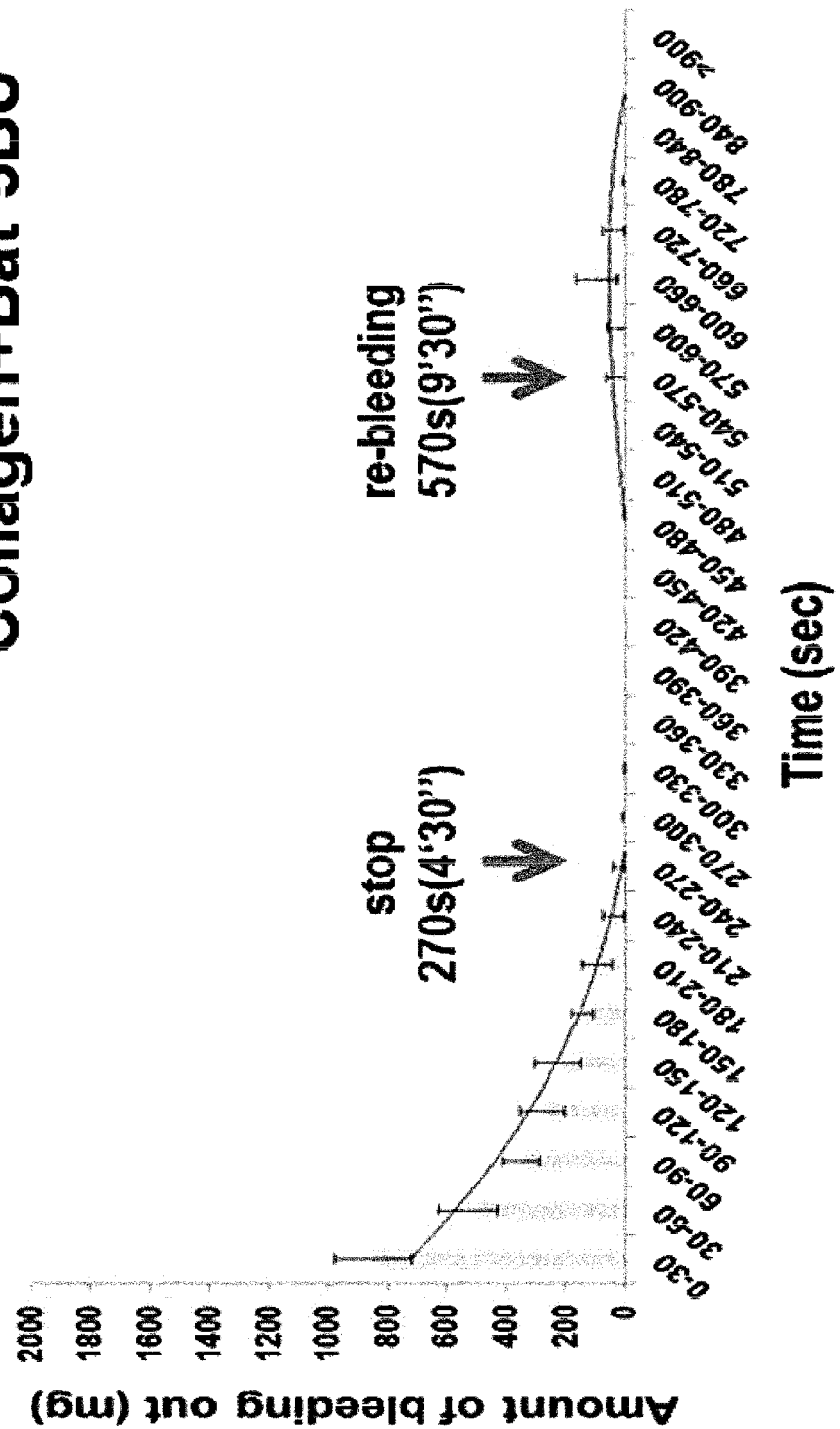
FIG. 4D illustrates a hemostatic effect and rebleeding measurement results when a combination of collagen and 5 BU of a recombinant batroxobin mixed composition is used in a femoral artery wound model. Experimental results are shown in a graph of an amount of bleeding out over time.
Figure 4E:
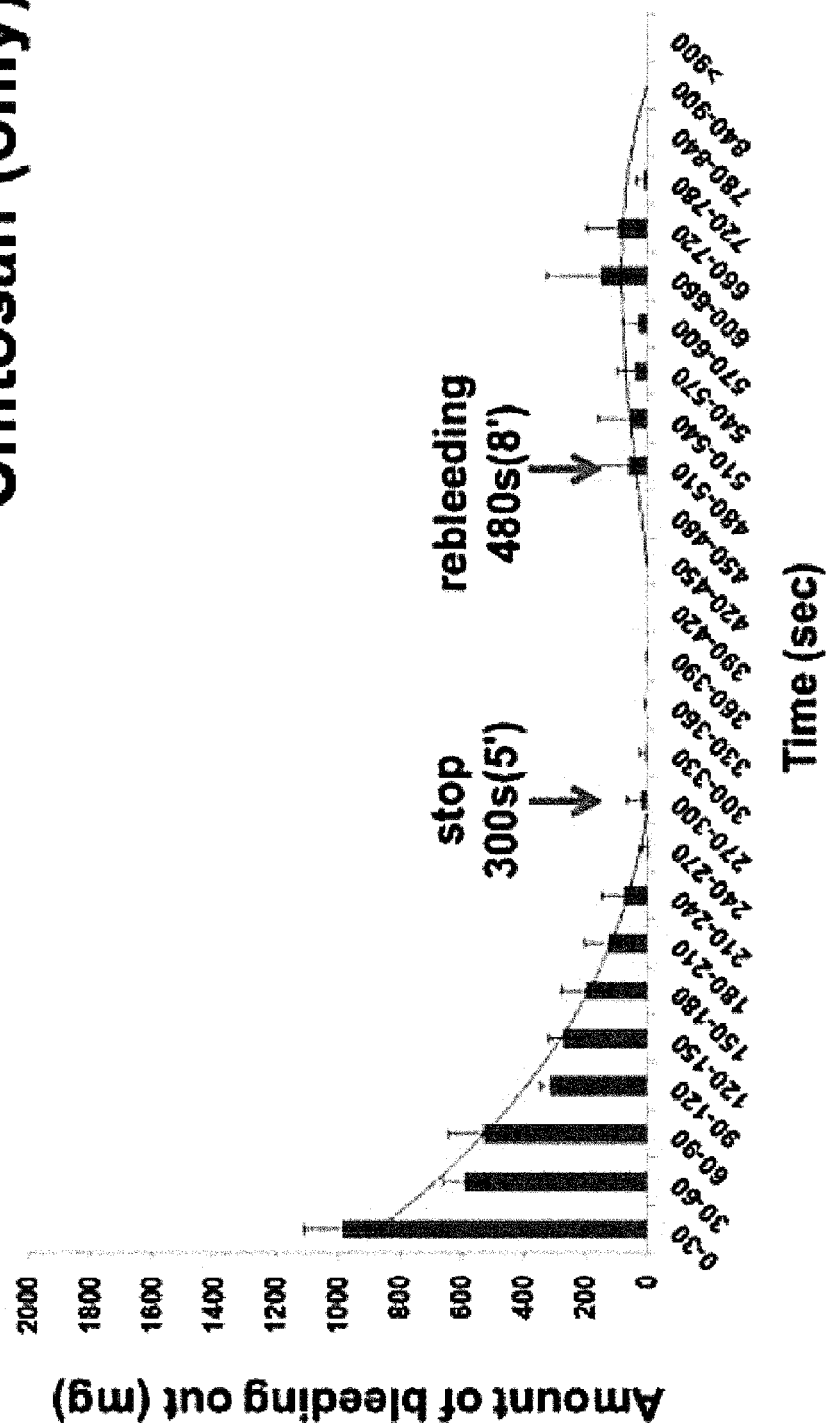
FIG. 4E illustrates a hemostatic effect and rebleeding measurement results when chitosan is used alone in a femoral artery wound model. Experimental results are shown in a graph of an amount of bleeding out over time.
Figure 4F:
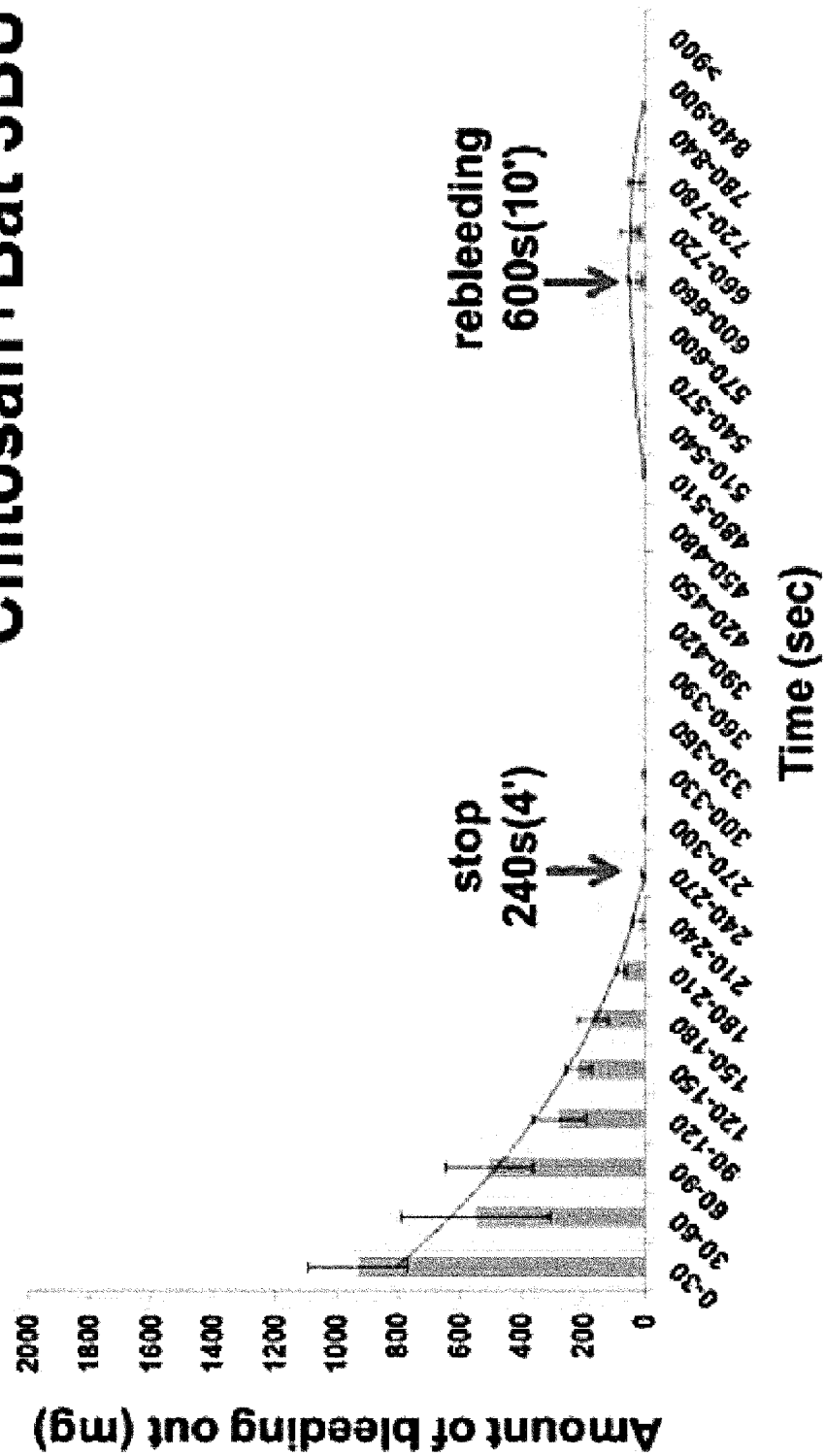
FIG. 4F illustrates a hemostatic effect and rebleeding measurement results when a combination of chitosan and 3 BU of a recombinant batroxobin mixed composition is used in a femoral artery wound model. Experimental results are shown in a graph of an amount of bleeding out over time.
Figure 4G:
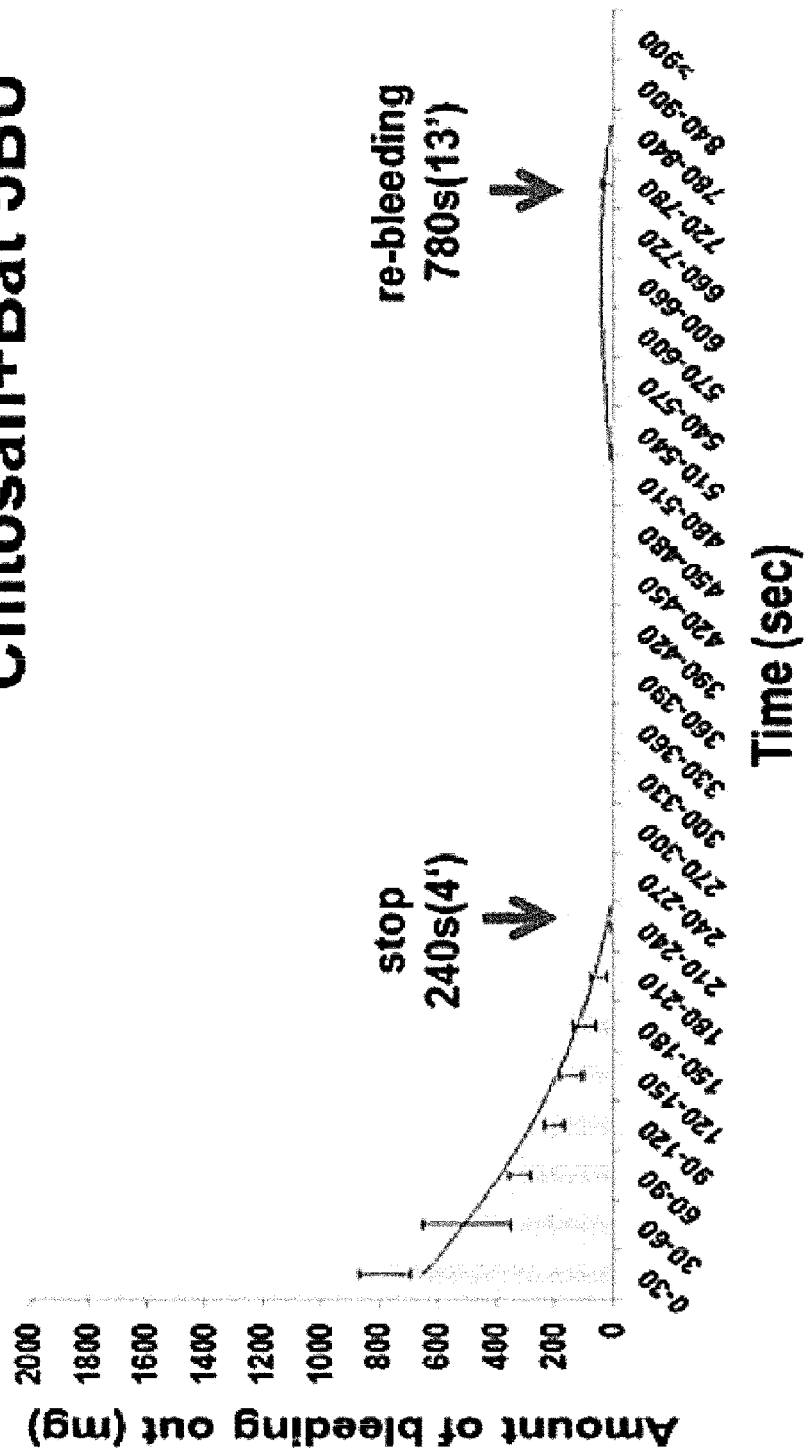
FIG. 4G illustrates a hemostatic effect and rebleeding measurement results when a combination of chitosan and 5 BU of a recombinant batroxobin mixed composition is used in a femoral artery wound model. Experimental results are shown in a graph of an amount of bleeding out over time.
Figure 4H:
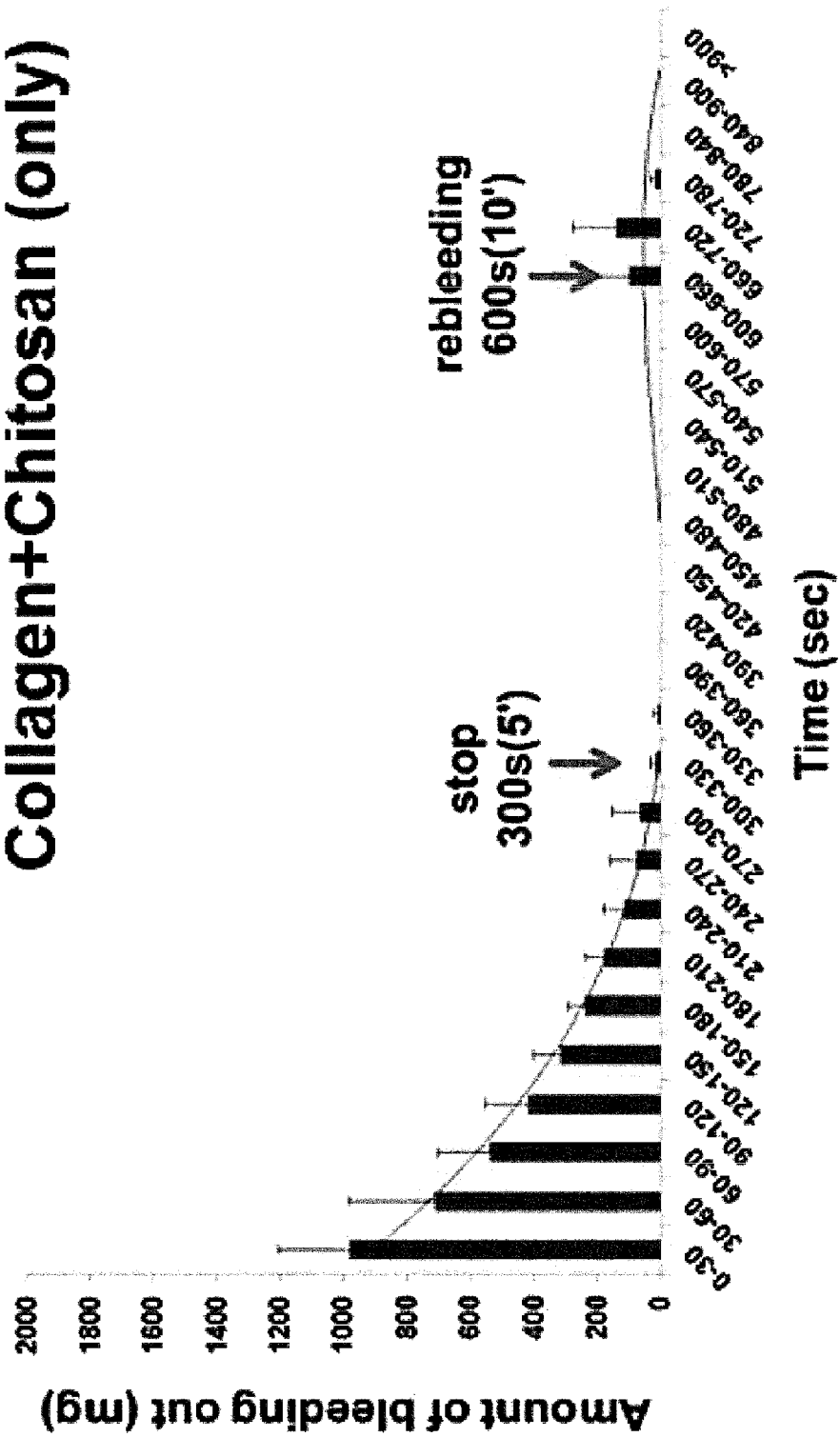
FIG. 4H illustrates a hemostatic effect and rebleeding measurement results when a combination of collagen and chitosan is used in a femoral artery wound model. Experimental results are shown in a graph of an amount of bleeding out over time.
Figure 4I:
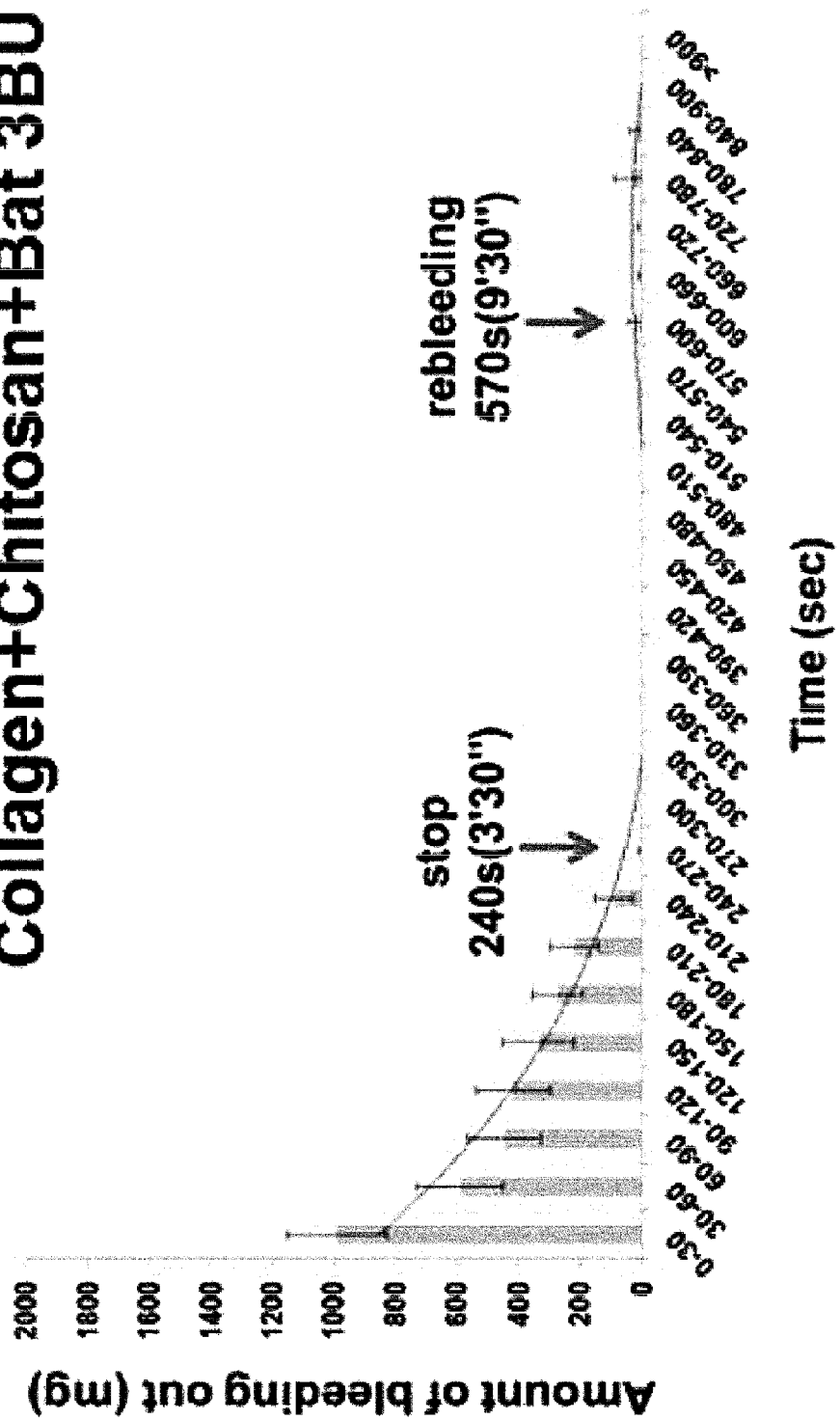
FIG. 4I illustrates a hemostatic effect and rebleeding measurement results when a combination of collagen, chitosan and 3 BU of a recombinant batroxobin mixed composition is used in a femoral artery wound model. Experimental results are shown in a graph of an amount of bleeding out over time.
Figure 4J:
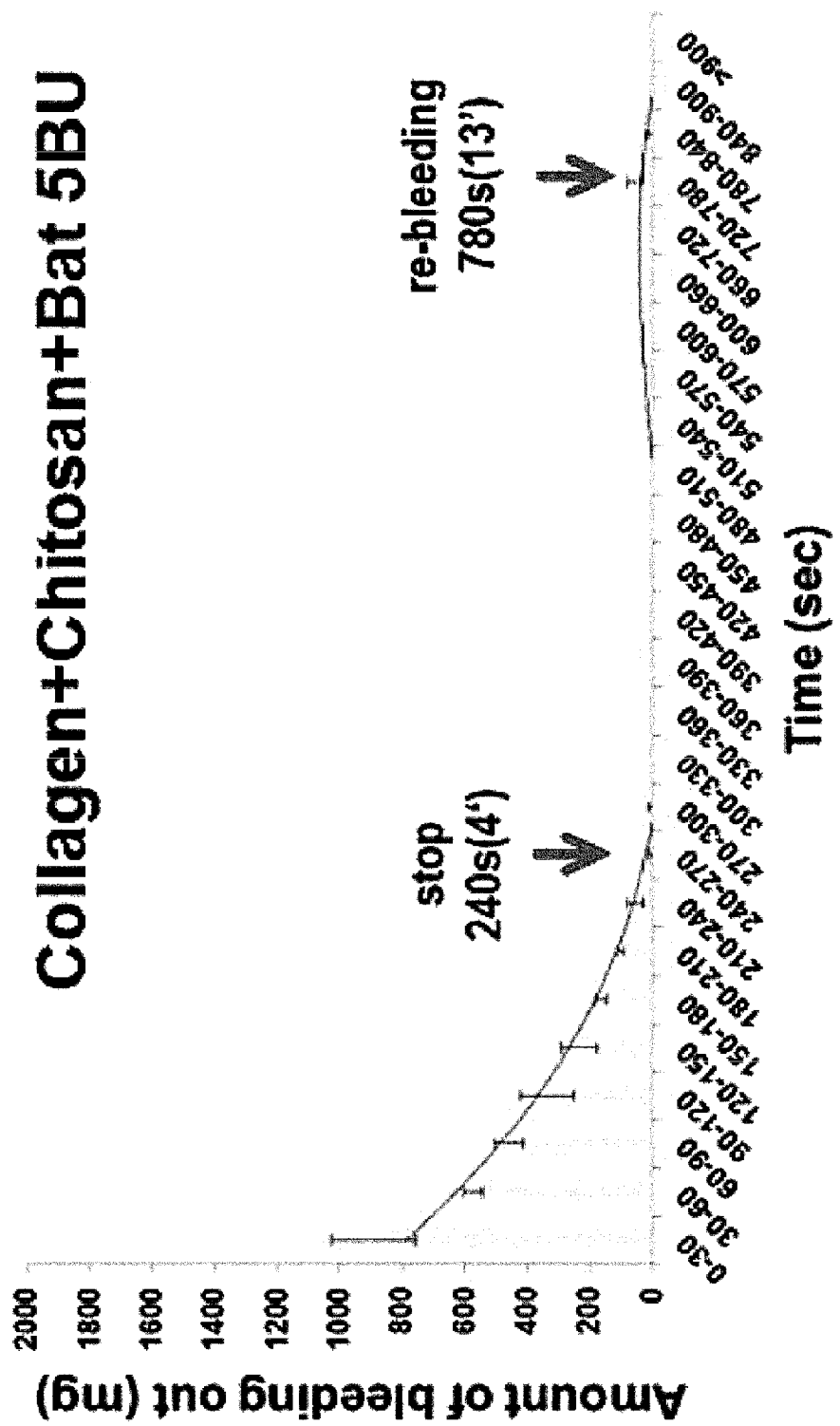
FIG. 4J illustrates a hemostatic effect and rebleeding measurement results when a combination of collagen, chitosan and 5 BU of a recombinant batroxobin mixed composition is used in a femoral artery wound model. Experimental results are shown in a graph of an amount of bleeding out over time.

A sprague-Dawley (SD) rat weighing about 200 g to 350 g was anesthetized using 30 mg/kg of Zoletil and 10 mg/kg of Rompun (Bayer, Canada), and limbs of the rat were fixed onto a styrofoam board and were tilted by about 45°. A left thigh part of the rat was incised, a fascia was cut out, and a femoral artery was exposed. Blood vessels were dissected using a surgical knife, a hemostatic pad was applied directly to a wound site, a filter paper (Whatman, a diameter of 4.25 mm) was applied to blood flowing immediately below the hemostatic pad at intervals of 10 seconds and a weight thereof was measured. Here, an amount of bleeding out was measured by subtracting a weight of only a filter paper from the weight of the filter paper stained with blood. When no further blood is absorbed onto a filter paper, bleeding was judged to stop, and a time at which the blood stopped was confirmed. (FIG. 4A).

For hemostatic pads, a non-treated group was used as a control group, and 9 groups except the control group were used. The 9 groups include 3 comparative groups (that is, a group containing 1% collagen, a group containing 1% chitosan and a group containing 1% collagen and 1% chitosan), and a group containing 3 BU of batroxobin in 1% collagen, a group containing 5 BU of batroxobin in 1% collagen, a group containing 3 BU of batroxobin in 1% chitosan, a group containing 5 BU of batroxobin in 1% chitosan, a group containing 3 BU of batroxobin in 1% collagen and 1% chitosan, and a group containing 5 BU of batroxobin in 1% collagen and 1% chitosan.

As a result, it was confirmed from graphs showing bleeding times that rebleeding occurred after initial hemostasis in all the groups. It was found that a point in time of initial hemostasis was shortened by about 30 seconds based on an increase in a concentration of batroxobin in comparison to the comparative groups. Also, it was confirmed that an amount of bleeding out in first 30 seconds was reduced by almost half in all the groups in comparison to the non-treated group. In other words, it was found amounts of bleeding out were reduced to about 50% at almost the same ratio in all the experimental groups. Among the experimental groups, the smallest amount of first-bleeding out were shown in the group containing 5 BU of batroxobin in collagen, the group containing 5 BU of batroxobin in chitosan and the group containing 5 BU of batroxobin in collagen and chitosan showed. Also, it was found that a point in time of rebleeding was delayed by about 3 minutes on average as the concentration of the batroxobin increases from 0 BU to 3 BU and 5 BU, and it was confirmed from graphs that a period of time of rebleeding was remarkably shortened (FIGS. 4B through 4J).

Figure 5A:
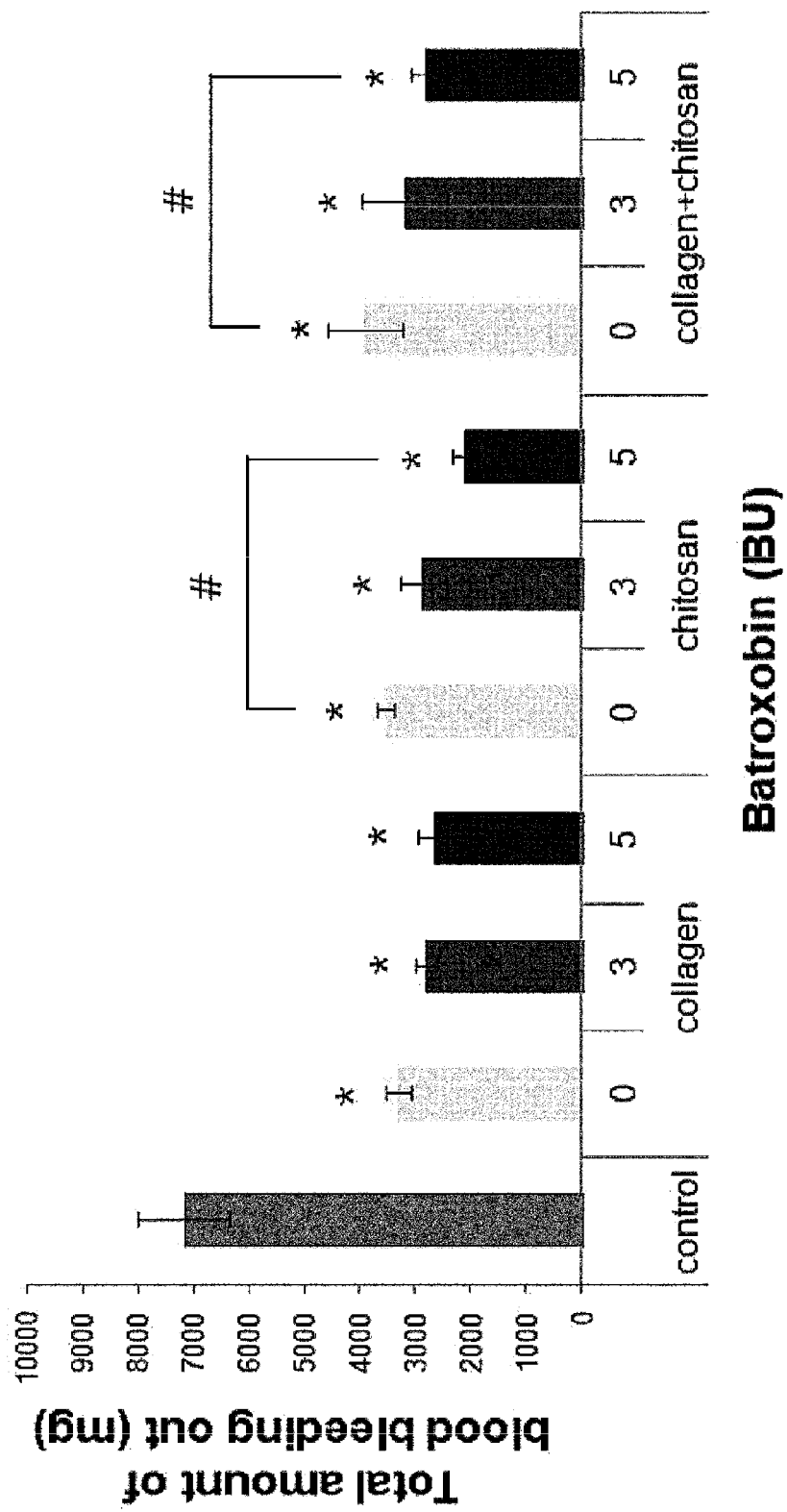
FIG. 5A illustrates results of measurement of a total amount of bleeding out in a femoral artery wound model.
Figure 5C:
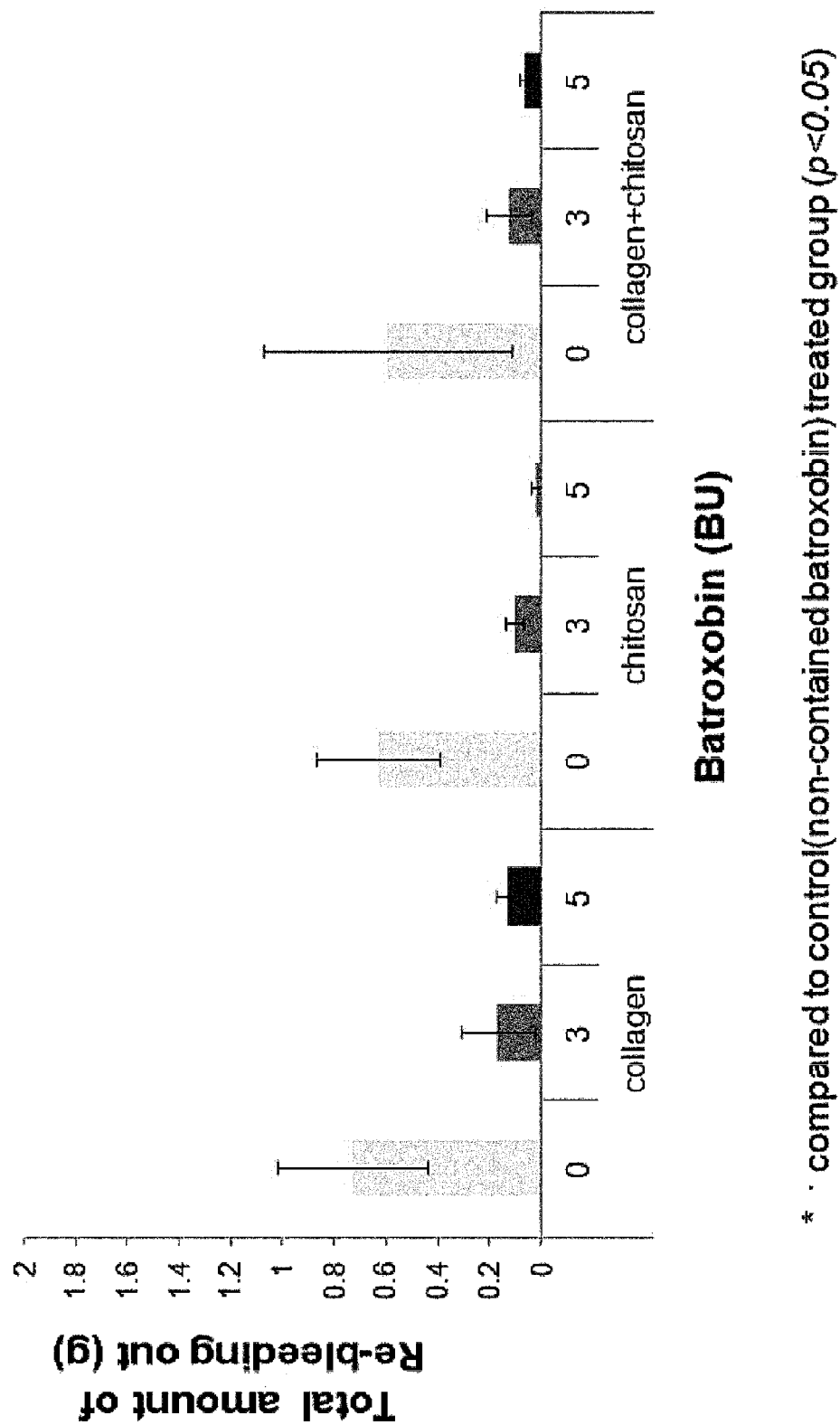
FIG. 5C illustrates results of measurement of an amount of rebleeding out in a femoral artery wound model.

The amounts of bleeding out were classified into a total amount of bleeding out, an amount of first-bleeding out and an amount of rebleeding out and were verified. In results showing the total amount of bleeding out, it was confirmed that the total amount of bleeding out in all the groups was about 50% lower than that of the control group, and that the amount of bleeding out decreased as the concentration of batroxobin in each of the comparative groups increases (FIG. 5A). Also, a graph for a comparison of an amount of first-bleeding out shows a decrease in the amount of bleeding out based on an increase in the concentration of batroxobin in comparison to the comparative groups treated with only collagen or only chitosan, however, significant effects were unknown except the group containing 5 BU of batroxobin in chitosan (FIG. 5B). However, in a graph to verify an amount of rebleeding out, small amounts of bleeding out were shown in all the experimental groups in comparison to the comparative groups, and it was evaluated through a statistical analysis thereof that all the experimental groups had significant effects. Also, it was confirmed that rebleeding was remarkably suppressed, in particular, in the group containing 5 BU of batroxobin in chitosan and the groups containing batroxobin in collagen and chitosan, in comparison to each of the comparative groups (FIG. 5C).

A bleeding stop time, a rebleeding time and a total amount of bleeding out were summarized as shown in Table 3 below. The bleeding stop time refers to a point in time at which no further blood was absorbed onto a filter paper, and the rebleeding time refers to a point in time at which blood was absorbed onto a filter paper.

TABLE 3

| Batroxobin(BU) | Control | Collagen | | | Chitosan |
|---|---|---|---|---|---|
| | | 0 | 3 | 5 | 0 |
| Bleeding stop time (sec) | >900 | 330 | 300 | 270 | 300 |
| Re-bleeding time (sec) | — | 480 | 510 | 570 | 480 |
| Total amount of blood bleeding out (mg) | 7188.4 ± 826.1 | 3301.3 ± 224.7 | 2792.9 ± 195.6 | 2713.3 ± 234.4 | 3538.6 ± 157.3 |
| Total amount of Re-bleeding out (mg) | | 731.9 ± 292.5 | 168.3 ± 141.4 | 133.9 ± 45.0 | 631.6 ± 242.6 |
| n | 4 | 4 | 4 | 4 | 4 |

| | Chitosan | | Collagen + Chitosan (1.1) | | |
|---|---|---|---|---|---|
| Batroxobin(BU) | 3 | 5 | 0 | 3 | 5 |
| Bleeding stop time (sec) | 240 | 240 | 300 | 240 | 240 |
| Re-bleeding time (sec) | 600 | 780 | 600 | 570 | 780 |

TABLE 3-continued

| | | | | | |
|---|---|---|---|---|---|
| Total amount of blood bleeding out (mg) | 2863.8 ± 413.9 | 2115.2 ± 226.7 | 3912.4 ± 679.9 | 3199.7 ± 762.8 | 2799.9 ± 263.2 |
| Total amount of Re-bleeding out (mg) | 103.9 ± 35.1 | 15.8 ± 27.3 | 597.9 ± 479.8 | 123.8 ± 86.2 | 66.1 ± 21.9 |
| n | 4 | 4 | 4 | 4 | 4 |

Thus, based on results from the above animal experiment, it was confirmed that a batroxobin mixture according to the present disclosure has an in vivo effect on an actual wound model as well as an in vitro effect by blood sampling. Also, it was found that the amount of first-bleeding out, the amount of rebleeding out and the time were considerably reduced in comparison to the control group, and it was found that an effect of 5 BU of batroxobin was higher than that of 3 BU of batroxobin in a wound model.

Example 9. Statistical Analysis

All measured values were expressed as mean±standard deviation. Differences in mean values of normal distribution data were assessed by Student's t-test, and P>0.05 was regarded as a statistical difference.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A recombinant batroxobin mixed composition comprising recombinant batroxobins, wherein a glycosylation structure is bound to the recombinant batroxobins, and the glycosylation structure has structure represented by the following Formulae 2-8:

[Formula 2]

[Formula 3]

[Formula 4]

[Formula 5]

[Formula 6]

[Formula 7]

[Formula 8]

in Formulae 2 to 8, M represents a mannose, and G represents an N-acetylglucosamine, and wherein the recombinant batroxobin comprises the amino acid sequence of SEQ ID NO: 2.

2. The recombinant batroxobin mixed composition of claim 1, wherein the glycosylation structure is bound to N-terminal amino acid residues at positions 146 and 225 of SEQ ID NO: 2.

3. The recombinant batroxobin mixed composition of claim 1, wherein a mean molecular weight of recombinant batroxobin molecules included in the recombinant batroxobin mixture ranges from 28 kDa to 31 kDa.

4. A hemostatic composition comprising the recombinant batroxobin mixed composition of claim 1.

5. The hemostatic composition of claim 4, wherein 0.5 batroxobin unit (BU) to 20 BU of the recombinant batroxobin mixed composition is included in the hemostatic composition.

6. The hemostatic composition of claim 4, further comprising a biocompatible polymer.

7. The hemostatic composition of claim 6, wherein the biocompatible polymer has a concentration of 0.5 mg/ml to 5 mg/ml.

8. The hemostatic composition of claim 6, wherein the biocompatible polymer is collagen, chitosan or a combination thereof.

9. The hemostatic composition of claim 6, wherein the hemostatic composition suppresses rebleeding.

10. The hemostatic composition of claim 6, wherein the hemostatic composition is in a form of a solution in an aqueous medium, a suspension, an emulsion, powders, powdered drugs, granules, a sponge, a pad, a patch or a film.

11. A method of preparing a recombinant batroxobin hemostatic composition, the method comprising contacting the recombinant batroxobin mixed composition of claim 1 with an acid solution.

12. The method of claim 11, wherein the acid solution has a pH of 1 to 6.

13. The method of claim 11, wherein the acid solution comprises a biocompatible polymer.

* * * * *

SEQUENCE LISTING

```
<160> NUMBER OF SEQ ID NOS: 14

<210> SEQ ID NO 1
<211> LENGTH: 696
<212> TYPE: DNA
<213> ORGANISM: Artificial Sequence
<220> FEATURE:
<223> OTHER INFORMATION: BatSmx
<220> FEATURE:
<221> NAME/KEY: CDS
<222> LOCATION: (1)..(693)

<400> SEQUENCE: 1 gtt att ggt ggt gat gaa tgt gat att aat gaa cat cca ttt ttg gca      48
Val Ile Gly Gly Asp Glu Cys Asp Ile Asn Glu His Pro Phe Leu Ala
1               5                   10                  15 ttt atg tac tac tct cca aga tac ttt tgt ggt atg act ttg att aac      96
Phe Met Tyr Tyr Ser Pro Arg Tyr Phe Cys Gly Met Thr Leu Ile Asn
            20                  25                  30 caa gaa tgg gtt ttg act gca gca cat tgt aac aga aga ttt atg aga     144
Gln Glu Trp Val Leu Thr Ala Ala His Cys Asn Arg Arg Phe Met Arg
        35                  40                  45 att cat ttg ggt aag cat gca ggt tct gtt gca aat tac gat gaa gtt     192
Ile His Leu Gly Lys His Ala Gly Ser Val Ala Asn Tyr Asp Glu Val
    50                  55                  60 gtt aga tac cca aag gaa aag ttt att tgt cca aat aag aag aag aat     240
Val Arg Tyr Pro Lys Glu Lys Phe Ile Cys Pro Asn Lys Lys Lys Asn
65                  70                  75                  80 gtt att act gat aag gat att atg ttg att aga ttg gat aga cca gtt     288
Val Ile Thr Asp Lys Asp Ile Met Leu Ile Arg Leu Asp Arg Pro Val
                85                  90                  95 aag aac tct gaa cat att gca cca ttg tct ttg cca tct aac cca cca     336
Lys Asn Ser Glu His Ile Ala Pro Leu Ser Leu Pro Ser Asn Pro Pro
            100                 105                 110
```

```
tct gtt ggt tct gtt tgt aga att atg ggt tgg ggt gca att act act        384
Ser Val Gly Ser Val Cys Arg Ile Met Gly Trp Gly Ala Ile Thr Thr
            115                 120                 125 tct gaa gat act tac cca gat gtt cca cat tgt gca aac att aac ttg        432
Ser Glu Asp Thr Tyr Pro Asp Val Pro His Cys Ala Asn Ile Asn Leu
130                 135                 140 ttt aat aat act gtt tgt aga gaa gca tac aat ggt ttg cca gca aag        480
Phe Asn Asn Thr Val Cys Arg Glu Ala Tyr Asn Gly Leu Pro Ala Lys
145                 150                 155                 160 act ttg tgt gca ggt gtt ttg caa ggt ggt att gat act tgt ggt ggt        528
Thr Leu Cys Ala Gly Val Leu Gln Gly Gly Ile Asp Thr Cys Gly Gly
            165                 170                 175 gat tct ggt ggt cca ttg att tgt aat ggt caa ttt caa ggt att ttg        576
Asp Ser Gly Gly Pro Leu Ile Cys Asn Gly Gln Phe Gln Gly Ile Leu
            180                 185                 190 tct tgg ggt tct gat cca tgt gca gaa cca aga aag cca gca ttt tac        624
Ser Trp Gly Ser Asp Pro Cys Ala Glu Pro Arg Lys Pro Ala Phe Tyr
            195                 200                 205 act aag gtt ttt gat tac ttg cca tgg att caa tct att att gca ggt        672
Thr Lys Val Phe Asp Tyr Leu Pro Trp Ile Gln Ser Ile Ile Ala Gly
210                 215                 220 aat aag act gca act tgt cca taa                                        696
Asn Lys Thr Ala Thr Cys Pro
225                 230
```

<210> SEQ ID NO 2
<211> LENGTH: 231
<212> TYPE: PRT
<213> ORGANISM: Artificial Sequence
<220> FEATURE:
<223> OTHER INFORMATION: Synthetic Construct

<400> SEQUENCE: 2

```
Val Ile Gly Gly Asp Glu Cys Asp Ile Asn Glu His Pro Phe Leu Ala
1               5                   10                  15

Phe Met Tyr Tyr Ser Pro Arg Tyr Phe Cys Gly Met Thr Leu Ile Asn
            20                  25                  30

Gln Glu Trp Val Leu Thr Ala Ala His Cys Asn Arg Arg Phe Met Arg
        35                  40                  45

Ile His Leu Gly Lys His Ala Gly Ser Val Ala Asn Tyr Asp Glu Val
    50                  55                  60

Val Arg Tyr Pro Lys Glu Lys Phe Ile Cys Pro Asn Lys Lys Lys Asn
65                  70                  75                  80

Val Ile Thr Asp Lys Asp Ile Met Leu Ile Arg Leu Asp Arg Pro Val
            85                  90                  95

Lys Asn Ser Glu His Ile Ala Pro Leu Ser Leu Pro Ser Asn Pro Pro
            100                 105                 110

Ser Val Gly Ser Val Cys Arg Ile Met Gly Trp Gly Ala Ile Thr Thr
            115                 120                 125

Ser Glu Asp Thr Tyr Pro Asp Val Pro His Cys Ala Asn Ile Asn Leu
        130                 135                 140

Phe Asn Asn Thr Val Cys Arg Glu Ala Tyr Asn Gly Leu Pro Ala Lys
145                 150                 155                 160

Thr Leu Cys Ala Gly Val Leu Gln Gly Gly Ile Asp Thr Cys Gly Gly
            165                 170                 175

Asp Ser Gly Gly Pro Leu Ile Cys Asn Gly Gln Phe Gln Gly Ile Leu
            180                 185                 190
```

```
Ser Trp Gly Ser Asp Pro Cys Ala Glu Pro Arg Lys Pro Ala Phe Tyr
            195                 200                 205
Thr Lys Val Phe Asp Tyr Leu Pro Trp Ile Gln Ser Ile Ile Ala Gly
    210                 215                 220
Asn Lys Thr Ala Thr Cys Pro
225                 230

<210> SEQ ID NO 3
<211> LENGTH: 696
<212> TYPE: DNA
<213> ORGANISM: Artificial Sequence
<220> FEATURE:
<223> OTHER INFORMATION: nBat
<220> FEATURE:
<221> NAME/KEY: CDS
<222> LOCATION: (1)..(693)

<400> SEQUENCE: 3 gtc att gga ggt gat gaa tgt gac ata aat gaa cat cct ttc ctt gca      48
Val Ile Gly Gly Asp Glu Cys Asp Ile Asn Glu His Pro Phe Leu Ala
1               5                  10                  15 ttc atg tac tac tct ccc cgg tat ttc tgt ggt atg act ttg atc aac      96
Phe Met Tyr Tyr Ser Pro Arg Tyr Phe Cys Gly Met Thr Leu Ile Asn
            20                  25                  30 cag gaa tgg gtg ctg acc gct gca cac tgt aac agg aga ttt atg cgc     144
Gln Glu Trp Val Leu Thr Ala Ala His Cys Asn Arg Arg Phe Met Arg
        35                  40                  45 ata cac ctt ggt aaa cat gcc gga agt gta gca aat tat gat gag gtg     192
Ile His Leu Gly Lys His Ala Gly Ser Val Ala Asn Tyr Asp Glu Val
    50                  55                  60 gta aga tac cca aag gag aag ttc att tgt ccc aat aag aaa aaa aat     240
Val Arg Tyr Pro Lys Glu Lys Phe Ile Cys Pro Asn Lys Lys Lys Asn
65                  70                  75                  80 gtc ata acg gac aag gac att atg ttg atc agg ctg gac aga cct gtc     288
Val Ile Thr Asp Lys Asp Ile Met Leu Ile Arg Leu Asp Arg Pro Val
                85                  90                  95 aaa aac agt gaa cac atc gcg cct ctc agc ttg cct tcc aac cct ccc     336
Lys Asn Ser Glu His Ile Ala Pro Leu Ser Leu Pro Ser Asn Pro Pro
            100                 105                 110 agt gtg ggc tca gtt tgc cgt att atg gga tgg ggc gca atc aca act     384
Ser Val Gly Ser Val Cys Arg Ile Met Gly Trp Gly Ala Ile Thr Thr
        115                 120                 125 tct gaa gac act tat ccc gat gtc cct cat tgt gct aac att aac ctg     432
Ser Glu Asp Thr Tyr Pro Asp Val Pro His Cys Ala Asn Ile Asn Leu
    130                 135                 140 ttc aat aat acg gtg tgt cgt gaa gct tac aat ggg ttg ccg gcg aaa     480
Phe Asn Asn Thr Val Cys Arg Glu Ala Tyr Asn Gly Leu Pro Ala Lys
145                 150                 155                 160 aca ttg tgt gca ggt gtc ctg caa gga ggc ata gat aca tgt ggg ggt     528
Thr Leu Cys Ala Gly Val Leu Gln Gly Gly Ile Asp Thr Cys Gly Gly
                165                 170                 175 gac tct ggg gga ccc ctc atc tgt aat gga caa ttc cag ggc att tta     576
Asp Ser Gly Gly Pro Leu Ile Cys Asn Gly Gln Phe Gln Gly Ile Leu
            180                 185                 190 tct tgg gga agt gat ccc tgt gcc gaa ccg cgt aag cct gcc ttc tac     624
Ser Trp Gly Ser Asp Pro Cys Ala Glu Pro Arg Lys Pro Ala Phe Tyr
        195                 200                 205 acc aag gtc ttt gat tat ctt ccc tgg atc cag agc att att gca gga     672
Thr Lys Val Phe Asp Tyr Leu Pro Trp Ile Gln Ser Ile Ile Ala Gly
    210                 215                 220 aat aaa act gcg act tgc ccg tga                                     696
Asn Lys Thr Ala Thr Cys Pro
225                 230
```

Asn Lys Thr Ala Thr Cys Pro
225                 230

<210> SEQ ID NO 4
<211> LENGTH: 231
<212> TYPE: PRT
<213> ORGANISM: Artificial Sequence
<220> FEATURE:
<223> OTHER INFORMATION: Synthetic Construct

<400> SEQUENCE: 4

Val Ile Gly Gly Asp Glu Cys Asp Ile Asn Glu His Pro Phe Leu Ala
1               5                   10                  15

Phe Met Tyr Tyr Ser Pro Arg Tyr Phe Cys Gly Met Thr Leu Ile Asn
            20                  25                  30

Gln Glu Trp Val Leu Thr Ala Ala His Cys Asn Arg Arg Phe Met Arg
        35                  40                  45

Ile His Leu Gly Lys His Ala Gly Ser Val Ala Asn Tyr Asp Glu Val
    50                  55                  60

Val Arg Tyr Pro Lys Glu Lys Phe Ile Cys Pro Asn Lys Lys Lys Asn
65                  70                  75                  80

Val Ile Thr Asp Lys Asp Ile Met Leu Ile Arg Leu Asp Arg Pro Val
                85                  90                  95

Lys Asn Ser Glu His Ile Ala Pro Leu Ser Leu Pro Ser Asn Pro Pro
            100                 105                 110

Ser Val Gly Ser Val Cys Arg Ile Met Gly Trp Gly Ala Ile Thr Thr
        115                 120                 125

Ser Glu Asp Thr Tyr Pro Asp Val Pro His Cys Ala Asn Ile Asn Leu
    130                 135                 140

Phe Asn Asn Thr Val Cys Arg Glu Ala Tyr Asn Gly Leu Pro Ala Lys
145                 150                 155                 160

Thr Leu Cys Ala Gly Val Leu Gln Gly Gly Ile Asp Thr Cys Gly Gly
                165                 170                 175

Asp Ser Gly Gly Pro Leu Ile Cys Asn Gly Gln Phe Gln Gly Ile Leu
            180                 185                 190

Ser Trp Gly Ser Asp Pro Cys Ala Glu Pro Arg Lys Pro Ala Phe Tyr
        195                 200                 205

Thr Lys Val Phe Asp Tyr Leu Pro Trp Ile Gln Ser Ile Ile Ala Gly
    210                 215                 220

Asn Lys Thr Ala Thr Cys Pro
225                 230

<210> SEQ ID NO 5
<211> LENGTH: 255
<212> TYPE: DNA
<213> ORGANISM: Artificial Sequence
<220> FEATURE:
<223> OTHER INFORMATION: SMF
<220> FEATURE:
<221> NAME/KEY: CDS
<222> LOCATION: (1)..(255)

<400> SEQUENCE: 5 atg aga ttt cca tct att ttt act gca gtt ttg ttt gca gca tct tct     48
Met Arg Phe Pro Ser Ile Phe Thr Ala Val Leu Phe Ala Ala Ser Ser
1               5                   10                  15 gca ttg gca gca cca gtt aac act act act gaa gat gaa act gca caa     96
Ala Leu Ala Ala Pro Val Asn Thr Thr Thr Glu Asp Glu Thr Ala Gln
            20                  25                  30

```
att cca gca gaa gca gtt att ggt tac tct gat ttg gaa ggt gat ttt        144
Ile Pro Ala Glu Ala Val Ile Gly Tyr Ser Asp Leu Glu Gly Asp Phe
            35                  40                  45 gat gtt gct gtt ttg cca ttt tct aac tct act aat aac ggt ttg ttg        192
Asp Val Ala Val Leu Pro Phe Ser Asn Ser Thr Asn Asn Gly Leu Leu
    50                  55                  60 ttt att aat act act att gca tct att gca gca aag gaa gaa ggt gtt        240
Phe Ile Asn Thr Thr Ile Ala Ser Ile Ala Ala Lys Glu Glu Gly Val
65                  70                  75                  80 tct ttg gaa aaa aga                                                    255
Ser Leu Glu Lys Arg
                85

<210> SEQ ID NO 6
<211> LENGTH: 85
<212> TYPE: PRT
<213> ORGANISM: Artificial Sequence
<220> FEATURE:
<223> OTHER INFORMATION: Synthetic Construct

<400> SEQUENCE: 6

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
                85

<210> SEQ ID NO 7
<211> LENGTH: 274
<212> TYPE: DNA
<213> ORGANISM: Artificial Sequence
<220> FEATURE:
<223> OTHER INFORMATION: cloning cassette for SMF

<400> SEQUENCE: 7
ggatccaaac gatgagattt ccatctattt ttactgcagt tttgtttgca gcatcttctg      60
cattggcagc accagttaac actactactg aagatgaaac tgcacaaatt ccagcagaag     120
cagttattgg ttactctgat tggaaggtg attttgatgt tgctgttttg ccatttttcta    180 actctactaa taacggtttg ttgtttatta atactactat tgcatctatt gcagcaaagg     240
aagaaggtgt ttctttggaa aaaagagcgg ccgc                                  274

<210> SEQ ID NO 8
<211> LENGTH: 40
<212> TYPE: DNA
<213> ORGANISM: Artificial Sequence
<220> FEATURE:
<223> OTHER INFORMATION: synthetic

<400> SEQUENCE: 8
taactctttt ttccaaagaa acaccttctt cctttgctgc                             40

<210> SEQ ID NO 9
<211> LENGTH: 24
```

```
<212> TYPE: DNA
<213> ORGANISM: Artificial Sequence
<220> FEATURE:
<223> OTHER INFORMATION: synthetic

<400> SEQUENCE: 9
ggatccaaac gatgagattt ccat                                            24

<210> SEQ ID NO 10
<211> LENGTH: 32
<212> TYPE: DNA
<213> ORGANISM: Artificial Sequence
<220> FEATURE:
<223> OTHER INFORMATION: synthetic

<400> SEQUENCE: 10
ctttggaaaa aagagttatt ggtggtgatg aa                                   32

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
gcggccgctt atggacaagt                                                 20

<210> SEQ ID NO 12
<211> LENGTH: 12
<212> TYPE: DNA
<213> ORGANISM: Artificial sequence
<220> FEATURE:
<223> OTHER INFORMATION: synthetic

<400> SEQUENCE: 12
gtatctctcg ag                                                         12

<210> SEQ ID NO 13
<211> LENGTH: 12
<212> TYPE: DNA
<213> ORGANISM: Artificial sequence
<220> FEATURE:
<223> OTHER INFORMATION: synthetic

<400> SEQUENCE: 13
gtttctttgg aa                                                         12

<210> SEQ ID NO 14
<211> LENGTH: 9
<212> TYPE: PRT
<213> ORGANISM: Artificial sequence
<220> FEATURE:
<223> OTHER INFORMATION: synthetic

<400> SEQUENCE: 14

Leu Glu Lys Arg Val Ile Gly Asp Glu
1               5
```